(12) United States Patent
Glorioso, III et al.

(10) Patent No.: US 12,414,973 B2
(45) Date of Patent: Sep. 16, 2025

(54) ANTIGENICALLY STEALTHED ONCOLYTIC VIRUSES

(71) Applicants: University of Pittsburgh—Of the Commonwealth System of Higher Education, Pittsburgh, PA (US); Trustees of the University of Pennsylvania, Philadelphia, PA (US)

(72) Inventors: Joseph C. Glorioso, III, Pittsburgh, PA (US); Gary H. Cohen, Havertown, PA (US); Doina Atanasiu, Norwood, PA (US); Tina Marie Cairns, Warminster, PA (US); Bonnie Lynn Hall, Allison Park, PA (US); Justus B. Cohen, Allison Park, PA (US); Ceren Tuzmen, Pittsburgh, PA (US)

(73) Assignees: University of Pittsburgh—Of the Commonwealth System of Higher Education, Pittsburgh, PA (US); The Trustees of the University of Pennsylvania, Philadelphia, PA (US)

( * ) Notice: Subject to any disclaimer, the term of this patent is extended or adjusted under 35 U.S.C. 154(b) by 1199 days.

(21) Appl. No.: 17/058,379

(22) PCT Filed: May 31, 2019

(86) PCT No.: PCT/US2019/034914
§ 371 (c)(1),
(2) Date: Nov. 24, 2020

(87) PCT Pub. No.: WO2019/232379
PCT Pub. Date: Dec. 5, 2019

(65) Prior Publication Data
US 2021/0121513 A1    Apr. 29, 2021

Related U.S. Application Data

(60) Provisional application No. 62/678,737, filed on May 31, 2018.

(51) Int. Cl.
*A61K 35/763*    (2015.01)
*C12N 7/00*    (2006.01)

(52) U.S. Cl.
CPC .............. *A61K 35/763* (2013.01); *C12N 7/00* (2013.01); *C12N 2710/16621* (2013.01); *C12N 2710/16622* (2013.01); *C12N 2710/16632* (2013.01); *C12N 2710/16645* (2013.01)

(58) Field of Classification Search
None
See application file for complete search history.

(56) References Cited

U.S. PATENT DOCUMENTS

| | | |
|---|---|---|
| 9,593,347 B2 | 3/2017 | Glorioso, III et al. |
| 2010/0172906 A1 | 7/2010 | Lai et al. |
| 2013/0096186 A1 | 4/2013 | Glorioso, III et al. |
| 2016/0250267 A1 | 9/2016 | Uchida et al. |
| 2017/0081384 A1 | 3/2017 | Cascio et al. |
| 2018/0002723 A1* | 1/2018 | Campadelli ............ C12N 15/86 |

OTHER PUBLICATIONS

Krummenacher et al., Structure of unliganded HSV gD reveals a mechanism for receptor-mediated activation of virus entry, The EMBO Journal, 2005, pp. 4144-4153, vol. 24, No. 23.
Kuan et al., Increased Binding Affinity Enhances Targeting of Glioma Xenografts by EGFRVIII-Specific scFv, Int. J. Cancer, 2000, pp. 962-969, vol. 88.
Lazear et al., Antibody-Induced Conformational Changes in Herpes Simplex Virus Blycoprotein gD Reveal New Targets for Virus Neutralization, Journal of Virology, 2012, pp. 1563-1576, vol. 86, No. 3, doi: 10.1128/JVI.06480-11.
Lee et al., Structural basis for the antibody neutralization of Herpes simplex virus, Acta Cryst., 2013, pp. 1935-1945, vol. D69, doi: 10.1107/S0907444913016776.
Lechner et al., Immunogenicity of murine solid tumor models as a defining feature of in vivo behavior and response to immunotherapy, J Immunother, 2013, pp. 477-489, vol. 36, No. 9, doi: 10.1097/01.cji.0000436722.46675.4a.
Liu et al., ICP34.5 deleted herpes simplex virus with enhanced oncolytic, immune stimulating, and anti-tumour properties, Gene Therapy, 2003, pp. 92-303, vol. 10, doi: 10.1038/sj.gt.3301885.
Lundstrom, New frontiers in oncolytic viruses: optimizing and selecting for virus strains with improved efficacy, Biologics: Targets and Therapy, 2018, pp. 43-60, vol. 12, doi: 10.2147/BTT.S140114.
MacDonald et al., Human herpesvirus 1 strain KOS, complete genome, May 10, 2012, GenBank: JQ673480.1.
MacDonald et al., Genome Sequence of Herpes Simplex Virus 1 Strain KOS, Journal of Virology, Jun. 2012, pp. 6371-6372, vol. 86, No. 11, doi: 10.1128/JVI.00646-12.
MacDonald et al., Human herpesvirus 1 strain Mckrae, partial genome, Aug. 23, 2012, GenBank: JX142173.1.
MacDonald et al., Genome Sequence of Herpes Simplex Virus 1 Strain McKrae, Journal of Virology, Sep. 2012, pp. 9540-9541, vol. 86, No. 17, doi: 10.1128/JVI.01469-12.
Manoj et al., Mutations in herpes simplex virus glycoprotein D that prevent cell entry via nectins and alter cell tropism, PNAS, Aug. 24, 2004, pp. 12414-12421, vol. 101, No. 34, doi: 10.1073ypnas.0404211101.
Marlin et al., Antigenic Variation (mar Mutations) in Herpes Simplex Virus Glycoprotein B Can Induce Temperature-Dependent Alterations in GB Processing and Virus Production, Journal of Virology, Jul. 1986, pp. 142-153, vol. 59, No. 1.
Mazzacurati et al., Use of MiRNA Response Sequences to Block Off-target Replication and Increase the Safety of an Unattenuated, Glioblastoma-targeted Oncolytic HSV, Molecular Therapy, Jan. 2015, pp. 99-107, vol. 23, No. 1, doi: 10.1038/mt.2014.177.
McGeoch et al., Human herpesvirus 1, complete genome, GenBank: NC_001806.1, Aug. 24, 2010.

(Continued)

*Primary Examiner* — Benjamin P Blumel
(74) *Attorney, Agent, or Firm* — The Webb Law Firm

(57) ABSTRACT

Provided herein are antigenically stealthed HSV particles, and methods of use of the antigenically-stealthed HSV particles.

21 Claims, 14 Drawing Sheets
Specification includes a Sequence Listing.

(56) References Cited

OTHER PUBLICATIONS

McGeoch et al., The Complete DNA Sequence of the Long Unique Region in the Genome of Herpes Simplex Virus Type 1, J. gen. Virol., 1988, pp. 1531-1574, vol. 69.
Miller et al., Development of a Syngenic Murine B16 Cell Line-Derived Melanoma Susceptible to Destruction by Neuroattenuated HSV-1, Molecular Therapy, Feb. 2001, pp. 160-168, vol. 3, No. 2, doi: 10.1006/mthe.2000.0240.
Minson et al., An Analysis of the Biological Properties of Monoclonal Antibodies against Glycoprotein D of Herpes Simplex Virus and Identification of Amino Acid Substitutions that Confer Resistance to Neutralization, J. gen. Virol., 1986, pp. 1001-1013, vol. 67.
Miyagawa et al., Herpes simplex viral-vector design for efficient transduction of nonneuronal cells without cytotoxicity, PNAS, Mar. 16, 2015, pp. E1632-1641, doi: 10.1073/pnas.1423556112.
Muggeridge et al., Antigenic and Functional Analysis of a Neutralization Site of HSV-1 Glycoprotein D, Virology, 1990, pp. 375-387, vol. 174.
Navarro et al., Domains of Herpes Simplex Virus I Glycoprotein B that Function in Virus Penetration, Cell-to-Cell Spread, and Cell Fusion, Virology, 1992, pp. 99-112, vol. 186.
Nelson, Antibody Fragments Hope and Hype, MAbs, 2010, pp. 77-83, vol. 2, No. 1, doi: 10.4161/mabs.2.1.10786.
Omidfar et al., Production of a Novel Camel Single-Domain Antibody Specific for the Type III Mutant EGFR, Tumor Biol, 2004, pp. 296-305, vol. 25, doi: 10.1159/000081395.
Overwijk et al., B16 as a Mouse Model for Human Melanoma, Current Protocols in Immunology, 2000, pp. 20.1.1-20.1.29, vol. 39, doi: 10.1002/0471142735.im2001s39.
Patriarca et al., Epithelial cell adhesion molecule expression (CD326) in cancer: A short review, Cancer Treatment Reviews, Feb. 2012, pp. 68-75, vol. 38, No. 1, doi: 10.1016/j.ctrv.2011.04.002.
Peters et al, Designing herpes viruses as oncolytics, Molecular Therapy—Oncolytics, 2015, vol. 2, doi: 10.1038/mto.2015.10.
Petrovic et al., Insertion of a ligand to HER2 in GB retargets HSV tropism and obviates the need for activation of the other entry glycoproteins, PLoS Pathogens, Apr. 19, 2017, e1006352, doi: 10.1371/journal.ppat.1006352.
Petrovic et al., Dual Ligand Insertion in GB and gD of Oncolytic Herpes Simplex Viruses for Retargeting to a Producer Vero Cell Line and to Cancer Cells, Journal of Virology, Mar. 2018, e02122-17, vol. 92, No. 6, doi: 10.1128/JVI.02132-17.
Pulaski et al., Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model, Cancer Research, May 15, 2000, pp. 2710-2715, vol. 60.
Rahman et al., Specific Depletion of Human Anti-adenovirus Antibodies Facilitates Transduction in an in Vivo Model for Systemic Gene Therapy, Molecular Therapy, May 2001, pp. 768-778, vol. 3, No. 5, doi: 10.1006/mthe.2001.0316.
Rehman et al., Into the clinic: Talimogene laherparepvec (T-VEC), a first-in-class intratumoral oncolytic viral therapy, Journal for Immuno Therapy of Cancer, 2016, vol. 4, No. 53, doi: 10.1186/s40425-016-0158-5.
Reinhart et al., Abstract 114: Replication-Defective HSC Vector Development for Targeted Gene Delivery, Molecular Therapy, May 2016, p. S48, vol. 24, No. 1.
Reinhart et al., An HSV-based library screen identifies PP1α as a negative TRPV1 regulator with analgesic activity in models of pain, Molecular Therapy—Methods & Clinical Development, 2016, vol. 3, doi: 10.1038/mtm.2016.40.
Remington: The Science and Practice of Pharmacy, 21st edition, 2005, Chapter 41, Lippincott, Williams & Wilkins.
Remington: The Science and Practice of Pharmacy, 21st edition, 2005, Chapter 42, Lippincott, Williams & Wilkins.
Sanchez-Pescador et al., Antibodies to Epitopes of Herpes Simplex Virus Type 1 Glycoprotein B (GB) in Human Sera: Analysis of Functional GB Epitopes Defined by Inhibition of Murine Monoclonal Antibodies, The Journal of Infectious Diseases, Oct. 1993, pp. 844-853, vol. 198, No. 4.
Saw et al., Using a Split Luciferase Assay (SLA) to measure the kinetics of cell-cell fusion mediated by herpes simplex virus glycoproteins, Methods., Nov. 15, 2015, pp. 68-75, vol. 90, doi: 10.1016/j.ymeth.2015.05.021.
Sisk et al., High-Level Expression and Purification of Secreted Forms of Herpes Simplex Virus Type 1 Glycoprotein gD Synthesized by Baculovirus-Infected Insect Cells, Journal of Virology, Feb. 1994; pp. 766-775, vol. 68, No. 2.
Straiton, Tumor-targeting protein could be future of personalized cancer therapy, BioTechniques, May 19, 2019, https://www.biotechniques.com/cancer-research/tumor-targeting-protein-could-be-future-of-personalized-cancer-therapy/.
Talmadge et al., Cancer metastasis is selective or random depending on the parent tumour population, Nature, Jun. 17, 1982, pp. 593-594, vol. 297.
Topalian et al., Safety, Activity, and Immune Correlates of Anti-PD-1 Antibody in Cancer, The New England Journal of Medicine, Jun. 28, 2012, pp. 2443-2454, vol. 366, No. 26.
Tsai et al., Impact of Human Neutralizing Antibodies on Antitumor Efficacy of an Oncolytic Adenovirus in a Murine Model, Clinical Cancer Research, Nov. 1, 2004, pp. 7199-7206, vol. 10, doi: 10.1158/1078-0432.CCR-04-0765.
Tuzmen, Improving EGFR-retargeted HSV resistance to neutralizing antibodies, Presented at University of Pittsburgh School of Medicine, Mar. 28, 2019.
Uchida et al., Generation of Herpesvirus Entry Mediator (HVEM)-Restricted Herpes Simplex Virus Type 1 Mutant Viruses: Resistance of HVEM-Expressing Cells and Identification of Mutations That Rescue Nectin-1 Recognition, Journal of Virology, Apr. 2009, pp. 2951-2961, vol. 83, No. 7, doi: 10.1128/JVI.01449-08.
Uchida et al., A Double Mutation in Glycoprotein GB Compensates for Ineffective gD-Dependent Initiation of Herpes Simplex Virus Type 1 Infection, Journal of Virology, Dec. 2010, pp. 12200-12209, vol. 84, No. 23, doi: 10.1128/JVI.01633-10.
Uchida et al., Novel Mutations in GB and gH Circumvent the Requirement for Known gD Receptors in Herpes Simplex Virus 1 Entry and Cell-to-Cell Spread., Journal of Virology, Feb. 2013, pp. 1430-1442, vol. 87, No. 3, doi: 10.1128/JVI.02804-12.
Uchida et al., Effective Treatment of an Orthotopic Xenograft Model of Human Glioblastoma Using an EGFR-retargeted Oncolytic Herpes Simplex Virus, Molecular Therapy, Mar. 2013, pp. 561-569, vol. 21, No. 3, doi: 10.1038/mt.2012.211.
Whitbeck et al., The Major Neutralizing Antigenic Site on Herpes Simplex Virus Glycoprotein D Overlaps a Receptor-Binding Domain, Journal of Virology, Dec. 1999, pp. 9879-9890, vol. 73, No. 12.
Whitbeck et al., Repertoire of Epitopes Recognized by Serum IgG from Human Vaccinated with Herpes Simplex Virus 2 Glycoprotein D, Journal of Virology, Jul. 2014, pp. 7786-7795, vol. 88, No. 14, doi: 10.1128/JVI.00544-14.
Wiesner et al., De novo Induction of Genetically Engineered Brain Tumors in Mice Using Plasmid DNA, Cancer Res., Jan. 15, 2009, pp. 431-439, vol. 69, No. 2, doi: 10.1158/0008-5472.CAN-08-1800.
Uchida et al, "Oncolytic Herpes Simplex Virus Vectors Fully Retargeted to Tumor-Associated Antigens", Current Cancer Drug Targets, 2018, pp. 162-170, vol. 18.
Abdiche et al., High-Throughput Epitope Binning Assays on Label-Free Array-Based Biosensors Can Yield Exquisite Epitope Discrimination That Facilitates the Selection of Monoclonal Antibodies With Functional Activity, PLoS One, Mar. 20, 2014, vol. 9, No. 3. e92451, doi: 10.1371/journal.pone.0092451,PMID: 24651868, PMCID: PMC3961344.
Abdiche et al., Assessing kinetic and epitopic diversity across orthogonal monoclonal antibody generation platforms, MAbs, 2016, pp. 264-277, vol. 8, No. 2, doi: 10.1080/19420862.2015.1118596, Epub Dec. 14, 2015, PMID: 26652308, PMCID: PMC4966639.
Agarwal et al., Predicting effective microRNA target sites in mammalian mRNAs, eLife, 2015, vol. 5, No. 4, e05005, doi: 10.7554/eLife.05005.
Akimoto et al., A new delivery system for 5-fluorouracil using prodrug and converting enzyme, Br. J. Ophtalmol, 2002, vol. 86, pp. 581-586.

(56) References Cited

OTHER PUBLICATIONS

Aslakson et al., Selective Events in the Metastatic Process Defined by Analysis of the Sequential Dissemination of Subpopulations of a Mouse Mammary Tumor, Cancer Research, Mar. 15, 1992, pp. 13-99-1405, vol. 52.

Atanasiu et al., Cascade of Events Governing Cell-Cell Fusion Induced by Herpes Simplex Virus Glycoproteins gD, gH/gL, and GB, Journal of Virology, Dec. 2010, p. 12292-12299, vol. 84, No. 23, doi: 10.1128/JVI.01700-10.

Atanasiu et al., Dual Split Protein-Based Fusion Assay Reveals that Mutations to Herpes Simplex Virus (HSV) Glycoprotein GB Alter the Kinetics of Cell-Cell Fusion Induced by HSV Entry Glycoproteins, Journal of Virology, Nov. 2013, pp. 11332-11345, vol. 87, No. 21.

Atanasiu et al., Regulation of Herpes Simplex Virus Glycoprotein-Induced Cascade of Events Governing Cell-Cell Fusion, Journal of Virology, Dec. 2016, pp. 10535-10544, vol. 90, No. 23, doi:10.1128/JVI.01501-16.

Atanasiu et al., Using Antibodies and Mutants to Localize the Presumptive gH/gL Binding Site on Herpes Simplex Virus gD, Journal of Virology, Dec. 2018, vol. 92, No. 24, e01694-18.

Belshe et al., Efficacy Results of a Trial of a Herpes Simplex Vaccine, N Engl J Med, Jan. 5, 2012, pp. 34-43, vol. 336, No. 1.

Belshe et al., Correlate of Immune Protection Against HSV-1 Genital Disease in Vaccinated Women, J Infect Dis, Mar. 15, 2014, pp. 828-836, vol. 209.

Bender et al., Antigenic and Mutational Analyses of Herpes Simplex Virus Glycoprotein B Reveal Four Functional Regions, Journal of Virology, Apr. 2007, pp. 3827-3841, vol. 81, No. 8, doi: 10.1128/JVL02710-06.

Cairns et al., Epitope Mapping of Herpes Simplex Virus Type 2 gH/gL Defines Distinct Antigenic Sites, Including Some Associated with Biological Function. J Virol, Mar. 2006, pp. 2596-2608, vol. 80, No. 6, doi: 10.1128/JVI80.6.2596-2608.2006.

Cairns et al., Mechanism of Neutralization of Herpes Simplex Virus by Antibodies Directed at the Fusion Domain of Glycoprotein B, J Virol, Mar. 2014, pp. 2677-2689, vol. 88, No. 5, doi: 10.1128/JVI.03200-13.

Cairns et al., Dissection of the antibody response against herpes simplex virus glycoproteins in naturally infected humans, 2014, J. Virol., pp. 12612-12622, vol. 88, No. 21, doi: 10.11.28/JVI.01930-14.

Cairns et al., Patient-specific neutralizing antibody responses to herpes simplex virus are attributed to epitopes on gD, GB, or both and can be type specific, J Virol, Sep. 2015, pp. 9213-9231, vol. 89, No. 18, doi: 10.1128/JVI.01213-15.

Cairns et al., Global Sensing of the Antigenic Structure of Herpes Simplex Virus gD Using High-Throughput Array-Based SPR Imaging, PLoS Pathog, Jun. 14, 2017, doi: 10.1371/journal.ppat.1006430.

Campadelli-Fiume et al., Retargeting Strategies for Oncolytic Herpes Simplex Viruses, Viruses, 2016, vol. 8, No. 63, doi: 10.3390/v8030063.

Carfi, et al., Herpes Simplex Virus Glycoprotein D Bound to the Human Receptor HveA, Molecular Cell, Jul. 2001, pp. 169-179, vol. 8.

Chahlavi et al., Effect of prior exposure to herpes simplex virus 1 on viral vector-mediated tumor therapy in Immunocompetent mice, Gene Therapy, 1999, pp. 1751-1758, vol. 6, doi: 10.1038/sj.gt.3301003.

Chowdary et al., Crystal structure of the conserved herpesvirus fusion regulator complex gH-gL, Nat Struct Mol Biol., Jul. 2010, pp. 882-888, vol. 17, No. 6, doi: 10.1038/nsmb.1837.

Chung et al., A compact synthetic pathway rewires cancer signaling to therapeutic effector release, Science, May 3, 2019, vol. 364, No. 6439, doi: 10.1126/science.aat6982.

Cohen, An Approach to Antigenically "Stealth" Oncolytic HSV to the Human Immune System, Presented at University of Pennsylvania, May 31, 2018.

Conner et al., A strategy for systemic delivery of the oncolytic herpes virus HSV1716: redirected tropism by anti- binding sites incorporated on the virion surface as a glycoprotein D fusion protein, Gene Therapy, 2008, pp. 1579-1592, vol. 15.

Cranage et al., Identification of the human cytomegalovirus glycoprotein B gene and induction of neutralizing antibodies via its expression in recombinant vaccinia virus, The EMBO Journal, 1986, pp. 3057-3063, vol. 5, No. 11.

Di Giovine et al., Structure of Herpes Simplex Virus Glycoprotein D Bound of the Human Receptor Nectin-1, PLoS Pathogens, Sep. 2011, vol. 7, No. 9, e1002277.

Eisenberg et al., Localization of Epitopes of Herpes Simplex Virus Type 1 Glycoprotein D, Journal of Virology, Feb. 1985, pp. 634-644, vol. 53, No. 2.

Eisenberg et al., Herpes Virus Fusion and Entry: A Story with Many Characters, Viruses, 2012, pp. 800-832, vol. 4, doi: 10.3390/v4050800.

Fidler, Selection of Successive Tumour Lines for Metastasis, Nature New Biology, Apr. 4, 1973, pp. 148-149, vol. 242.

Forrer et al., A novel strategy to design binding molecules harnessing the modular nature of repeat proteins, FEBS Letters, 2003, pp. 2-6, vol. 539.

Fu et al., Construction of an Oncolytic Herpes Simplex Virus That Precisely Targets Hepatocellular Carcinoma Cells, Molecular Therapy, Feb. 2012, pp. 339-346, vol. 20, No. 2, doi: 10.1038/mt.2011.265.

Gatta et al., The Engineering of a Novel Ligand in gH Confers to HSV an Expanded Tropism Independent of gD Activation by Its Receptors, PLOS Pathogens, May 21, 2015, vol. 1, No. 5, e1004907,. doi: 10.1371/journal.ppat.1004907.
Gaur et al., Characterization of MicroRNA Expression Levels and Their Biological Correlates in Human Cancer Cell ines, Cancer Res, Mar. 15, 2007, pp. 2456-2468, vol. 67, No. 6, doi: 10.1158/0008-5472.CAN-06-2698.
Gebauer et al., Engineered protein scaffolds as next-generation antibody therapeutics, Current Opinion in Chemical Biology, 2009, pp. 245-255, vol. 13, doi: 10.1016/j.cbpa.2009.04.627.
Giavazzi et al., Syngeneic Murine Metastasis Models: B16 Melanoma, Methods in Molecular Biology, 2014, pp. 131-140, vol. 1070, doi: 10.1007/978-1-4614-8244-4_10.
Goins et al., Retargeting of Herpes Simplex Virus (HSV) Vectors, Curr Opin Virol., Dec. 2016, pp. 93-101, vol. 21, doi: 10.1016/j.coviro.2016.08.007.
Grandi et al., Design and application of oncolytic HSV vectors for glioblastoma therapy, Expert Rev Neurother., Apr. 2009; pp. 505-517, vol. 9, No. 4, doi: 10.1586/ern.09.9.
Greig, Talimogene Laherparepvec: First Global Approval, Drugs, 2016, pp. 147-154, vol. 76, doi: 10.1007/s40265-015-0522-7.
Gu et al., Escape of Hepatitis C Virus from Epitope I Neutralization Increases Sensitivity of Other Neutralization Epitopes, J Virol, May 2018, vol. 92, No. 9, e02066-17, doi: 10.1128/JVI.02066-17.
Harrington et al., Efficacy and safety of talimogene laherparepvec versus granulocyte-macrophage colony-stimulating factor in patients with stage IIIB/C and IVM1a melanoma: subanalysis of the Phase III OPTiM trial,Onco Targets and Therapy, 2016, pp. 7081-7093 , vol. 9, doi: 10.2147/OTT.S115245.
Hart, The Selection and Characterization of an Invasive Variant of the B16 Melanoma, Am J Pathol., Dec. 1979, pp. 587-600, vol. 97, No. 3, PMID: 507192, PMCID: PMC2042430.
Heldwein et al., Crystal Structure of Glycoprotein B from Herpes Simplex Virus 1, Science, Jul. 14, 2006, pp. 217-220, vol. 313, No. 5784, doi: 10.1126/science.1125721, PMID: 16840698.
Hensley et al., Hemagglutinin Receptor Binding Avidity Drives Influenza A Virus Antigenic Drift, Science, Oct. 30, 2009, pp. 734-736, vol. 326, No. 5953, doi: 10.1126/science.1178258 ,PMID: 19900932, PMCID: PMC2784927.
Highlander et al., Identification of mar Mutations in Herpes Simplex Virus Type 1 Glycoprotein B Which Alter Antigenic Structure and Function in Virus Penetration, Journal of Virology, Feb. 1989, pp. 730-738, vol. 63, No. 2.
Hodi et al., Improved Survival with Ipilimumab in Patients with Metastatic Melanoma, N Engl J Med, Aug. 19, 2010, pp. 711-723, vol. 363, No. 8, doi: 10.1056/NEJMoa1003466.
Holland et al., Physical Mapping of the Mutation in an Antigenic Variant of Herpes Simplex Virus Type 1 by Use of an Immunoreactive Plaque Assay, J Virol, May 1983, pp. 649-652, vol. 46, No. 2.

(56) References Cited

OTHER PUBLICATIONS

Isola et al., Fine Mapping of Antigenic Site II of Herpes Simplex Virus Glycoprotein D, J Virol, May 1989, pp. 2325-2334, vol. 63, No. 5.
Kaufman et al., Local and Distant Immunity Induced by Intralesional Vaccination with an Oncolytic Herpes Virus Encoding GM-CSF in Patients with Stage IIIc and IV Melanoma, Ann Surg Oncol, 2010, pp. 718-730, vol. 17, doi: 10.1245/s10434-009-0809-6.
Kaufman et al., Systemic versus local responses in melanoma patients treated with talimogene laherparepvec from a multi-institutional phase II study, JJournal for Immunotherapy of Cancer, 2016, vol. 4, No. 12, doi: 10.1186/s40425-016-0116-2.
Kousoulas et al., Antibody-Resistant Mutations in Cross-Reactive and Type-Specific Epitopes of Herpes Simplex Virus 1 Glycoprotein B Map in Separate Domains, Virology, 1988, pp. 423-431, vol. 166.
Wickstrand et al., Monoclonal Antibodies against EGFRvIII Are Tumor Specific and React with Breast and Lung Carcinomas and Malignant Gliomas, Cancer Research, Jul. 15, 1995, pp. 3140-3148, vol. 55.
Yewdell et al., Selection of Influenze A Virus Adsorptive Mutants by Growth in the Presence of a Mixture of Monoclonal Antihemag-glutinin Antibodies, Journal of Virology, Feb. 1986, pp. 623-628, vol. 57, No. 2.
Yoon, Mutations in the N Termini of Herpes Simplex Virus Type 1 and 2 gDs Alter Functional Interactions with the Entry/Fusion Receptors HVEM, Nectin-2, and 3-O-Sulfated Heparan Sulfate but Not with Nectin-1, Journal of Virology, Sep. 2003, pp. 9221-9231, vol. 77, No. 17, doi: 10.1128/JVI.77.17.9221-9231.2003.

\* cited by examiner

```
gD1     KYALADASLKMADPNRFRGKDLPVLDQLTDPPGVRRVYHIQAGLPDPFQPPSLPITVYYA  60
gD2     KYALADPSLKMADPNRFRGKNLPVLDQLTDPPGVKRVYHIQPSLEDPFQPPSIPITVYYA  60
        ****.********:*********** **** .* *****:***** gD1     VLERACRSVLLNAPSEAPQIVRGASEDVRKQPYNLTIAWFRMGGNCAIPITVMEYTECSY  120
gD2     VLERACRSVLLHAPSEAPQIVRGASDEARKHTYNLTIAWYRMGDNCAIPITVMEYTECPY  120
        *********.********:  :.*****:*.************** * gD1     NKSLGACPIRTQPRWNYYDSFSAVSEDNLGFLMHAPAFETAGTYLRLVKINDWTEITQFI  180
gD2     NKSLGVCPIRTQPRWSYYDSFSAVSEDNLGFLMHAPAFETAGTYLRLVKINDWTEITQFI  180
        ***.****.******************************************* gD1     LEHRAKGSCKYALPLRIPPSACLSPQAYQQGVTVDSIGMLPRFIPENQRTVAVYSLKIAG  240
gD2     LEHRARASCKYALPLRIPPAACLTSKAYQQGVTVDSIGMLPRFIPENQRTVALYSLKIAG  240
        ***:.********:*.:.:***********************.***** gD1     WHGPKAPYTSTLLPPELSETPNATQPELAPEDPEDSALLEDPVGTVAPQIPPNWHIPSIQ  300
gD2     WHGPKPPYTSTLLPPELSDTTNATQPELVPEDPEDSALLEDPAGTVSSQIPPNWHIPSIQ  300
        ***.**********:* *****.**********.*    ********* gD1     DAATPYHPPATPNNMGLIAGAVGGSLLAALVICGIVYWMHRRTRKAPKRIRLPHIREDDQ  360
gD2     DVA-PHHAPAAPSNPGLIIGALAGSTLAVLVIGGIAFWVRRRAQMAPKRLRLPHIRDDDA  359
        *.*  *:*.**:*.* *** ** ** **.*** **.:* **:: ****:******:**

gD1     PSSHQPLFY  369
gD2     PPSHQPLFY  368
        *.*******
```

*FIG. 1A*

```
gB1    mhqgapswgrrwfvvwallgltlgvlv---asaaptspgtpgvaa-atqaanggpatpap    56
gB2    mrgg------g--l---icalvvgalvaavasaapaapaaprasgawptvanggpasrpp    49
       *: *            :   : .*.:*.   ***::*..*  .:.    .******:  * gB1    pplgaaptgdpkpkknkkpknptpprpagdnatvaaghatlrehlrdikaentdanfyvc   116
gB2    pvpspattkarkrktkkppkrpeatpppdanatvaaghatlrahlreikvenadaqfyvc   109
       *  . * *      * *.:* **.*    * . ************ ***:**.**:**:****

gB1    ppptgatvvqfeqprrcptrpegqnytegiavvfkeniapykfkatmyykdvtvsqvwfg   176
gB2    ppptgatvvqfeqprrcptrpegqnytegiavvfkeniapykfkatmyykdvtvsqvwfg   169
       ************************************************************ gB1    hrysqfmgifedrapvpfeevidkinakgvcrstakyvrnnlettafhrddhetdmelkp   236
gB2    hrysqfmgifedrapvpfeevidkinakgvcrstakyvrnnmettafhrddhetdmelkp   229
       ***************************************:**************** gB1    anaatrtsrgwhttdlkynpsrveafhrygttvnciveevdarsvypydefvlatgdfvy   296
gB2    akvatrtsrgwhttdlkynpsrveafhrygttvnciveevdarsvypydefvlatgdfvy   289
       *:.********************************************************* gB1    mspfygyregshtehttyaadrfkqvdgfyardlttkaratapttrnllttpkftvawdw   356
gB2    mspfygyregshtehttyaadrfkqvdgfyardlttkaratspttrnllttpkftvawdw   349
       ***************************************:**************** gB1    vpkrpsvctmtkwqevdemlrseyggsfrfssdaisttfttnlteyplsrvdlgdcigkd   416
gB2    vpkrpavctmtkwqevdemlraeyggsfrfssdaisttfttnltqyslsrvdlgdcigrd   409
       ***:***********:*******************: * ***********:* gB1    ardamdrifarrynathikvgqpqyyqanggfliayqpllsntlaelyvrehlreqsrkp   476
gB2    areaidrmfarkynathikvgqpqyylatggfliayqpllsntlaelyvreymreqdrkp   469
       :.:.*:************  *.*****************:.*.**** gB1    pnptpppp--gasanasverikttssiefarlqftynhiqrhvndmlgrvaiawcelqnh   534
gB2    rnatpaplrerpsanasverikttssiefarlqftynhiqrhvndmlgriavawcelqnh   529
        * ** *       ***************************************:*:*******
```

*FIG. 1B*

```
gB1    eltlwnearklnpnaiasvtvgrrvsarmlgdvmavstcvpvaadnvivqnsmrissrpg    594
gB2    eltlwnearklnpnaiasatvgrrvsarmlgdvmavstcvpvapdnvivqnsmrvssrpg    589
       ****************.******************* ******:*** gB1    acysrplvsfryedqgplveggqlgennelrltrdaiepctvghrryftfgggyvyfeeya    654
gB2    tcysrplvsfryedqgplmegqlgennelrltrdalepctvghrryfifgggyvyfeeya    649
       :***************:***************:****** ******** gB1    yshqlsradittvstfidlnitmledhefvplevytrheikdsglldytevqrrnqlhdl    714
gB2    yshqlsradvttvrtfidlnitmledhefvplevytrheikdsglldytevqrrnqlhdl    709
       *******:*.********************************************** gB1    rfadidtvihadanaamfaglgaffegmgdlgravgkvvmgivggvvsavsgvssfmsnp    774
gB2    rfadidtviradanaamfaglcaffegmgdlgravgkvvmgvvggvvsavsgvssfmsnp    769
       *******:*******.***************:**************** gB1    fgalavgllvlaglaaaffafryvmrlqsnpmkalypplttkelknptnpdasge---gee    831
gB2    fgalavgllvlaglvaaffafryvlqlqrnpmkalypplttkelktsdpggvggegeegae    829
       ************.****:: ************.   ...   *  * gB1    ggdfdeaklaearemirymalvsamertehkakkkgtsallsakvtdmvmrkrrntnytq    891
gB2    gggfdeaklaearemirymalvsamertehkarkkgtsallsskvtnmvlrkrnkarysp    889
       **.*****************************:*********:***:**:***.::.*:

gB1    vpnkdgdadeddl    904
gB2    lhnedeagdedel    902
       : *:*  .***:*
```

FIG. 1C gD:scEΔ38

MGGAAARLGAVILFVVIVGLHGVRS

KDILMTQSPLSLPVSLGDQASISCRSSQNIVHNNGITYLEWYLQRPGQSPKLLIYKVSDR
FSGVPDRFSGSGSGTDFTLKISRVEAEDLGIYYCFQGSHIPPTFGGGTKLEIKRAAGGGG
SGGGGSGGGGSQVQLQQSGSEMARPGASVKLPCKASGDTFTSYWMHWVKQRHGHGPEWIG
NIYPGSGGTNYAEKFKNKVTLTVDRSSRTVYMHLSRLTSEDSAVYYCTRSGGPYFFDYWG
QGTTLTVSSGGGGSGSLDQLTDPPGVRRV*HIQAGLPDPFQPPSLPITVYYAVLERACRSV
LLNAPSEAPQIVRGASEDVRKQPYNLTIAWFRMGGNCAIPITVMEYTECSYNKSLGACPIR
TQPRWNYYDSFSAVSEDNLGFLMHAPAFETAGTYLRLVKINDWTEITQFILEHRAKGSCKY
ALPLRIPPSACLSPQAYQQGVTVDSIGMLPRFIPENQRTVAVYSLKIAGWHGPKAPYTSTL
LPPELSETPNATQPELAPEDPEDSALLEDPVGTVAPQIPPNWHIPSIQDAATPYHPPATPN
NMGLIAGAVGGSLLAALVICGIVYWMHRRTRKAPKRIRLPHIREDDQPSSHQPLFY

*FIG. 1D*

DILMTQSPLSLPVSLGDQASISCRSSQNIVHNNGITYLEWYLQRPGQSPKLLIYKVSDRF
SGVPDRFSGSGSGTDFTLKISRVEAEDLGIYYCFQGSHIPPTFGGGTKLEIKRAAGGG
GSGGGGSGGGGSQVQLQQSGSEMARPGASVKLPCKASGDTFTSYWMHWVKQRHG
HGPEWIGNIYPGSGGTNYAEKFKNKVTLTVDRSSRTVYMHLSRLTSEDSAVYYCTRSG
GPYFFDYWGQGTTLTVSS

ANTIGENICALLY STEALTHED ONCOLYTIC VIRUSES

CROSS REFERENCE TO RELATED APPLICATIONS

This application is the United States national phase of International Application No. PCT/US2019/034914 filed May 31, 2019, and claims the benefit of U.S. Provisional Patent Application No. 62/678,737 filed May 31, 2018, the disclosures of which are hereby incorporated by reference in their entirety.

STATEMENT REGARDING FEDERAL FUNDING

This invention was made with government support under Grant No. AI018289-38 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_2005635_ST25.txt. The size of the text file is 31,820 bytes, and the text file was created on Nov. 17, 2020.

Oncolytic viruses (OVs) have been created from a wide variety of virus species with considerable effort devoted to achieving vector safety and efficacy. Many have been tested in human clinical trials with varying success. Vector delivery has largely relied on intratumoral inoculation without restricting off-target cell infection. A limitation of intratumoral inoculation is that many tumors cannot be inoculated, for instance due to the size or location of the tumor, and further, disseminated metastasized cells and micrometastases often cannot easily be treated locally unless individually identifiable and limited in number.

We have previously developed oncolytic herpes simplex virus (oHSV) vectors that uniquely require a tumor-associated receptor for infection, such as the epidermal growth factor receptor (EGFR) or its tumor-specific variant, EGFRvIII (see, e.g., Uchida, H. et al. Effective treatment of an orthotopic xenograft model of human glioblastoma using an EGFR-retargeted oncolytic herpes simplex virus. Mol Ther 21, 561-569, doi:10.1038/mt.2012.211 (2013)). The engineering of retargeted oHSV has also been described in Campadelli-Fiume et al. (Retargeting strategies for oncolytic herpes simplex viruses. Viruses 8, 63, doi:10.3390/v8030063 (2016)). These "retargeted" oHSV can home to tumors bearing the target receptor in immune-compromised mice, but retargeted vectors have not yet been tested in patients or HSV-immune animal tumor models and it is likely that anti-HSV immunity, prevalent in the human population, will limit the effectiveness of oHSV tumor therapies.

As such, a substantial impediment to use of oHSVs is host immunity to HSV and, in particular, an adaptive immune response to antigens, e.g. epitopes or antigenic determinants, present in the oHSV particle. Sera from HSV-immune animals and patients effectively neutralize HSV by antibody-mediated mechanisms (see, e.g., Cairns, T. M., et al. 2015. Patient-specific neutralizing antibody responses to herpes simplex virus are attributed to epitopes on gD, gB, or both and can be type specific. *J Virol* 89:9213-9231). Major targets of these antibodies are two viral envelope glycoproteins, gD and gB, that are essential for HSV entry into cells. Adaptive host immunity can be developed either from an earlier HSV infection with virions comprising cross-reactive epitopes, or from earlier oHSV treatments with the same, or antigenically cross-reactive virus particles. Consequently, dissemination of virions injected systemically or replicated at the injection (tumor) site, to reach other tumors, or metastasized cells in a patient is expected to be, at best, transient due to pre-existing immunity or development of immunity post-injection.

Recombinant HSV vectors (virus particles) capable of systemic tumor homing in HSV-immune patients are desirable. Successful development of this novel type of oHSV will provide a generation of OVs suitable for systemic treatment of metastatic cancer, the central problem in cancer therapy.

SUMMARY

In one aspect of the invention, a retargeted herpes simplex virus (HSV) particle is provided. The virus particle comprises a genome, a capsid, tegument, and an envelope comprising a glycoprotein modified to reduce or eliminate recognition by antibodies that interfere with virus infection by blocking virus attachment and/or entry into a susceptible host cell.

In another aspect, a retargeted herpes simplex virus (HSV) particle is provided. The virus particle comprising an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated.

In another aspect, a recombinant HSV genome, comprising a nucleic acid encoding a retargeted herpes simplex virus (HSV) particle comprising a genome, a capsid, tegument, and an envelope comprising a glycoprotein modified to reduce or eliminate recognition by antibodies that interfere with virus infection by impairing or blocking virus attachment and/or entry into a susceptible host cell. In one embodiment, the virus particle comprises an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated.

In yet another aspect, a viral stock is provided, comprising at least $10^5$ pfus, at least $10^6$ pfus, at least $10^7$ pfus, at least $10^8$ pfus, at least $10^9$ pfus, at least $10^{10}$ pfus, or at least $10^{11}$ pfus of retargeted herpes simplex virus (HSV) particles comprising a genome, a capsid, tegument, and an envelope comprising a glycoprotein modified to reduce or eliminate recognition by antibodies that interfere with virus infection by impairing or blocking virus attachment and/or entry into a susceptible host cell. In one embodiment, the virus particles comprise an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated.

A dosage form comprising at least $10^5$ pfus, at least $10^6$ pfus, at least $10^7$ pfus, at least $10^8$ pfus, at least $10^9$ pfus, at least $10^{10}$ pfus, or at least $10^{11}$ pfus of retargeted herpes simplex virus (HSV) particles comprising a genome, a capsid, tegument, and an envelope comprising a glycoprotein modified to reduce or eliminate recognition by antibodies that interfere with virus infection by impairing or blocking virus attachment and/or entry into a susceptible host cell, and a pharmaceutically-acceptable excipient. In one embodiment, the virus particles comprise an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated, and a pharmaceutically-acceptable excipient.

A method of treating a patient having a cancer, comprising administering to the patient an amount of retargeted herpes simplex virus (HSV) particles effective to treat a cancer patient. The retargeted herpes simplex virus (HSV) particles comprise a genome, a capsid, tegument, and an envelope comprising a glycoprotein modified to reduce or eliminate recognition by antibodies that interfere with virus infection by impairing or blocking virus attachment and/or entry into a susceptible host cell, and a pharmaceutically-acceptable excipient. In one embodiment, the virus particles comprise an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated, and a pharmaceutically-acceptable excipient.

The following numbered clauses describe various aspects of the invention

Clause 1: A retargeted herpes simplex virus (HSV) particle, comprising a genome, a capsid, tegument, and an envelope comprising a glycoprotein modified to reduce or eliminate recognition by antibodies that interfere with virus infection by impairing or blocking virus attachment and/or entry into a susceptible host cell.

Clause 2: The virus particle of clause 1, comprising an antigenically-modified glycoprotein B (gB) and/or an antigenically-modified glycoprotein D (gD) protein, wherein one or more major epitopes of gB and/or gD reactive with one or more major human serum HSV-neutralizing antibodies is modified to reduce or eliminate binding of the virus particle to a major human serum HSV-neutralizing antibody such that neutralization of the virus by a major human serum HSV-neutralizing antibody is reduced or eliminated.

Clause 3: The virus particle of clause 2, wherein one or more epitopes of gD are modified to reduce or eliminate binding of the virus particle to a major human serum HSV-neutralizing antibody such that neutralization of the virus by the one or more major human serum HSV-neutralizing antibody is reduced or eliminated.

Clause 4: The virus particle of clause 2, wherein one or more epitopes of gB are modified to reduce or eliminate binding of the virus particle to a major human serum HSV-neutralizing antibody such that neutralization of the virus by the one or more major human serum HSV-neutralizing antibody is reduced or eliminated.

Clause 5: The virus particle of any one of clauses 1-3, wherein one or more of amino acids 10-20, 54, 75-79, 132, 140, 213, 216, 222-224, and 262-279 of SEQ ID NO: 1 or SEQ ID NO: 2, or one or more amino acids corresponding to amino acids 10-20, 54, 75-79, 132, 140, 213, 216, 222-224, and 262-279 of SEQ ID NO: 1 or SEQ ID NO: 2, are modified in the gD glycoprotein of the virus particle to reduce binding of a major HSV serum neutralizing antibody to the viral particle.

Clause 6: The virus particle of clause 5, wherein one or both of amino acids P54 and T213 of SEQ ID NO: 1 or SEQ ID NO: 2, or one or both amino acids corresponding to amino acids P54 and T213 of SEQ ID NO: 1 or SEQ ID NO: 2 are modified, such as P54Q and/or T213M.

Clause 7: The virus particle of clause 2, wherein one of more of amino acids 47, 62, 85, 203, 303, 304, 305, 308, 328, 335, 419, 473, 594, or 640-670 of SEQ ID NO: 3 or amino acid 412 of SEQ ID NO: 4, or one or more amino acids corresponding to amino acids 47, 62, 85, 203, 303, 304, 305, 308, 328, 335, 419, 473, 594, or 640-670 of SEQ ID NO: 3 or amino acid 412 of SEQ ID NO: 4, are modified in the gB glycoprotein of the virus particle to reduce binding of a major HSV serum neutralizing antibody to the viral particle.

Clause 8: The virus particle of any one of clauses 1-7, having a Δ38 mutation of SEQ ID NO: 1 or 2, or a mutation in a gD glycoprotein corresponding to a Δ38 mutation of SEQ ID NO: 1 or 2.

Clause 9: The virus particle of any one of clauses 1-8, comprising a non-native ligand capable of binding a surface component of a target cell type.

Clause 10: The virus particle of clause 9, wherein the target cell type is a cancer cell.

Clause 11: The virus particle of clause 9, wherein the non-native ligand capable of binding a surface component of a target cell type is incorporated into a viral envelope glycoprotein of the virus particle.

Clause 12: The virus particle of clause 11, wherein the viral envelope glycoprotein of the virus particle into which the ligand is incorporated is gD, gC, gB and/or gH.

Clause 13: The virus particle of clause 9, wherein the surface component is one or more of EGFR, EGFRvIII, other oncogenic EGFR variants, HERZ 00133, CXCR4, carcinoembryonic antigen (CEA). CLC-3/annexin-2/MMP-2, human transferrin receptor, EpCAM, or c-Met.

Clause 14: The virus particle of any one of clauses 1-13, wherein binding of at least one or more viral envelope glycoproteins to its natural receptor is eliminated.

Clause 15: The virus particle of any one of clauses 1-14, wherein the genome comprises an exogenous expression cassette.

Clause 16: The virus particle of clause 15, wherein the exogenous expression cassette encodes an agent that enhances tumor killing activity.

Clause 17: The virus particle of any one of clauses 1-16, wherein the genome comprises a target sequence for one or more microRNAs.

Clause 18: A recombinant HSV genome encoding the virus particle of any one of clauses 1-17.

Clause 19: A viral stock, comprising at least $10^5$ pfus, at least $10^6$ pfus, at least $10^7$ pfus, at least $10^8$ pfus, at least $10^9$ pfus, at least $10^{10}$ pfus, or at least $10^{11}$ pfus of a virus particle of any one of clauses 1-17.

Clause 20: A dosage form comprising at least $10^5$ pfus, at least $10^6$ pfus, at least $10^7$ pfus, at least $10^8$ pfus, at least $10^9$ pfus, at least $10^{10}$ pfus, or at least $10^{11}$ pfus of a virus particle of any one of clauses 1-17, and a pharmaceutically-acceptable excipient.

Clause 21: The dosage form of clause 20, provided as a unit dosage form.

Clause 22: The dosage form of clause 20, formulated for parenteral delivery.

Clause 23: The dosage form of clause 22, formulated for intravenous delivery.

Clause 24: A method of treating a patient having a cancer, comprising administering to the patient an amount of the virus particle of any one of clauses 1-17 effective to treat a cancer patient.

BRIEF DESCRIPTION OF THE DRAWINGS

FIG. 1A provides aligned exemplary sequences of HSV gD1 and gD2 (SEQ ID NOS: 1 and 2, respectively). Amino acids 2-24 may be replaced with the an scFv sequence, such as the sequence of FIG. 2, or other targeting ligand sequence. FIGS. 1B and 1C provides continuous aligned exemplary sequences of HSV gB1 and gB2 (SEQ ID NOS: 3 and 4, respectively). FIG. 1D provides the sequence of the modified ("retargeted") gD1, gD:scEΔ38 (SEQ ID NO: 5), having the anti-EGFR scFv sequence between residues 1 and 25, and a deletion of residue Y38 (438; denoted by a * in the amino acid sequence). The signal peptide (bold text) is shown on a separate line, but is a contiguous sequence with the remainder of the protein prior to its cleavage by signal peptidase.

(FIG. 6A) Time course of fusion activity relative to gD:scEΔ38 activity at 6 h (set to 100% luminescence). (FIGS. 6B and 6C) Antibody inhibition was performed by preincubation of the effector cell populations with MC5 (FIG. 6B) or MC23 mAb (FIG. 6C) at the indicated concentrations for 1 h prior to mixing with target cells. Data are shown relative to no antibody at 6 h (100%).

(FIG. 7A) Retargeted KNTc viruses produced by BAC transfection of Vero cells were used to infect Vero (nectin-1+/EGFR+), B78-H1, B78/C (nectin-1+), and B78-vIII cells (EGFRvIII+) at MOI=1 for 20 h. Viruses are identified at the top of the columns according to their retargeted gD version. Entry was recorded as mCherry fluorescence. (FIG. 7B) Western blots showing VP16, gD and gB content of equal genome copies of purified virions. Size markers in kDa are indicated at the left for the gD blot.

Figures 2, 3:
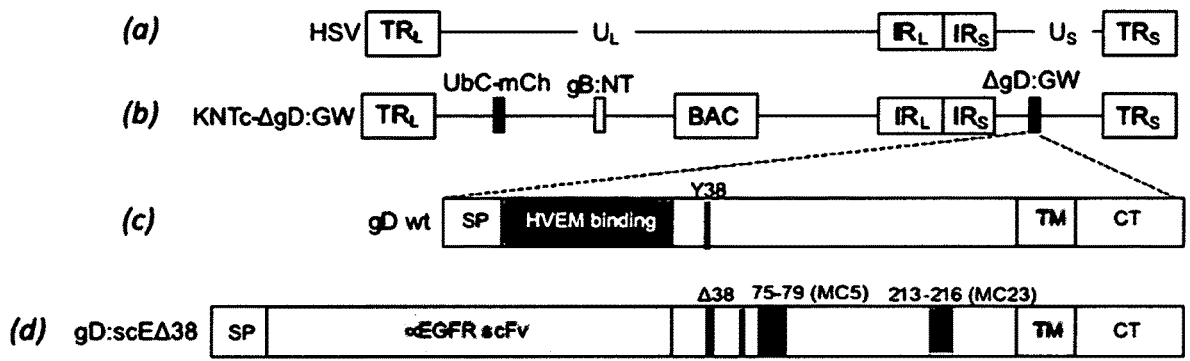
FIG. 2 provides an exemplary amino add sequence of an anti-EGFR/EGFRvIII scFv (SEQ ID NO: 6).
FIG. 3 shows schematically the genome structures of wt HSV (a) and KNTc recombinants. (b) KNTc-ΔgD:GW contains bacterial artificial chromosome (BAC) sequences between $U_L37$ and $U_L38$ for viral genome propagation and engineering in E. coli, a ubiquitin C promoter-mCherry expression cassette (UbC-mCh) between $U_L3$ and $U_L4$, two viral entry-enhancing mutations in the gB gene (gB:NT), and a GW recombination cassette in place of the gD coding sequence (ΔgD:GW) to allow rapid, orientation-specific insertion of reference and modified gD genes under control of the gD promoter. Inserted genes include wt gD1 (gD wt) (c) and retargeted gD (gD:scEΔ38) (d) without or with P54Q and/or T213M mutations. Known epitope residues for mAbs MC5 and MC23 are indicated above the gD:scEΔ38 schematic and mutated residues below.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to human beings.

An "effective amount" or "amount effective" to achieve a desirable therapeutic, pharmacological, medicinal, or physiological effect is any amount that achieves the stated purpose. Based on the teachings provided herein, one of ordinary skill can readily ascertain effective amounts of the elements of the described dosage form and produce a safe and effective dosage form and drug product.

In the context of delivery of therapeutic agents, such as the rHSV described herein, delivery profiles may be varied depending on the desired therapeutic effect. The nature of the present disclosure relates to delivery of a recombinant virus particle to cancer cells. As such, the therapeutic agent may preferably be delivered parenterally, such as intravenously. A "dosage form" is the physical form of a dose of a chemical compound used as a drug or medication intended for administration or consumption. A dosage form corresponds to a unit dosage form, even when dispensed from a drug product that includes multiple doses.

The virus particles may be incorporated into an intravenous or other parenteral dosage form which may comprise a pharmaceutically acceptable carrier, or excipient. Therapeutic/pharmaceutical compositions are prepared in accordance with acceptable pharmaceutical procedures, such as described in *Remington: The Science and Practice of Pharmacy,* 21st edition, ed. Paul Beringer et al., Lippincott, Williams & Wilkins, Baltimore, MD Easton, Pa. (2005) (see, e.g., Chapters 41 and 42 for examples of parenteral and intravenous formulations and methods of making such formulations). Depending on the delivery route, the dosage form may comprise additional carriers or excipients, such as water, saline (e.g., normal saline), or phosphate-buffered saline, as are broadly-known in the pharmaceutical arts. Compositions may comprise a pharmaceutically acceptable carrier, or excipient. An excipient is an inactive substance used as a carrier for the active ingredients of a medication. Although "inactive," excipients may facilitate and aid in increasing the delivery, stability or bioavailability of an active ingredient in a drug product. Non-limiting examples of useful excipients include: anti-adherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

The term "ligand" refers to a binding moiety for a specific target, its binding partner. The molecule can be a cognate receptor, a protein, a small molecule, a hapten, or any other relevant molecule, such as an affibody or a paratope-containing molecule. The term "antibody" refers to an immunoglobulin, derivatives thereof which maintain specific binding ability, and proteins having a binding domain which is homologous or largely homologous to an immunoglobulin binding domain. As such, the antibody operates as a ligand for its cognate antigen, which can be virtually any molecule.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', $F(ab')_2$, Fv, Fd, dsFv, scFv, diabody, triabody, tetrabody, di-scFv (dimeric single-chain variable fragment), bi-specific T-cell engager (BiTE), single-domain antibody (sdAb), or antibody binding domain fragments. In the context of targeting ligands, the antibody fragment may be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Ligands also include other engineered binding reagents, such as affibodies and designed ankyrin repeat proteins (DARPins), that exploit the modular nature of repeat proteins (Forrer T, Stumpp M T, Binz H K, Plückthun A: A novel strategy to design binding molecules harnessing the modular nature of repeat proteins, FEBS Lett 2003, 539: 2-6; Gebauer A, Skerra A: Engineered protein scaffolds as next-generation antibody therapeutics, Curr Opin Chem Biol 2009, 13:245-255), comprising, often as a single chain, one or more antigen-binding or epitope-binding sequences and at a minimum any other amino acid sequences needed to ensure appropriate specificity, delivery, and stability of the composition (see also, e.g., Nelson, A L, "Antibody Fragments Hope and Hype" (2010) MAbs 2(1):77-83).

A virus genome is a nucleic acid that can be packaged in a viral capsid and delivered as part of a virus particle. A viral genome includes any sequences necessary for packaging and delivery of the genome to a target cell for expression of one or more genes encoded by the viral genome. In the context of the HSV virus particles or virions described herein, the genome is packaged in the HSV viral capsid for delivery to target cells.

A significant amount of research has been directed to recombinant, oncolytic HSV viruses (oHSV). Methods of making and using oHSV vectors and viruses are broadly-known (see, e.g., Goins, W F, et al. Retargeting of Herpes Simplex Virus (HSV) Vectors *Curr Opin Virol.* 2016 December; 21: 93-101; Grandi, P, et al. Design and application of oncolytic HSV vectors for glioblastoma therapy. *Expert Rev Neurother.* 2009 April; 9(4): 505-517; and Peters and Rabkin, Designing herpes viruses as oncolytics, *Oncolytics* (2015) 2, 15010, incorporated herein by reference for their technical disclosure). Likewise, the overall structure of various HSV components are well-studied. In 2015, an oHSV (T-VEC, IMLYGIC™, talimogene laherparepvec) became the first oHSV to receive FDA approval based on its proven safety and efficacy in the treatment of melanoma patients. The effectiveness of this virus has relied in part on vector arming with granulocyte macrophage colony stimulating factor (GM-CSF) to enhance the recruitment of antigen presenting cells. However, as indicated above, implementation has, in part, been hampered by development of immunity to HSV, e.g. to HSV glycoproteins gB and gD. Following intra-tumor delivery of T-VEC for treatment of melanoma tumors, there was no correlation between anti-HSV antibody titers and therapeutic responses, but all seronegative patients seroconverted within 3-4 weeks. A large fraction of the human population is HSV seropositive and systemic treatment of metastatic cancer with even tumor-targeted HSV will likely be impaired in these patients. As such, a "stealthed" HSV, e.g., an oHSV that is concealed from pre-existing immunity, is described herein.

Amino acid sequences of exemplary HSV gB and gD glycoproteins are provided in FIGS. 1A-1C (SEQ ID NOS: 1-4). A number of studies have produced detailed epitope maps for of HSV gD and gB (see, e.g., Atanasiu D, et al. 2018. Using Antibodies and Mutants to Localize the Presumptive gH/gL Binding Site on Herpes Simplex Virus gD. *J Virol* 92:e01694-18; Cairns, T. M., et al. 2015. *J Virol* 89:9213-9231; Bender F C, et al. 2007. Antigenic and mutational analyses of herpes simplex virus glycoprotein B reveal four functional regions. J Virol 81(8):3827-3841; and Cairns T M, et al. 2006. Epitope Mapping of Herpes Simplex Virus Type 2 gH/gL Defines Distinct Antigenic Sites, Including Some Associated with Biological Function. *J Virol* 80:2596-2608; and Cairns T M, et al. (2017) Global Sensing of the Antigenic Structure of Herpes Simplex Virus gD Using High-Throughput Array-Based SPR Imaging. *PLoS Pathog* 13(6):e1006430 (Cairns et al. 2017)), including a more detailed understanding of the function of major serum antibody binding sites, including the relationship of the binding sites to viral neutralization, receptor binding, viral entry, and membrane fusion.

A "neutralizing antibody" is an antibody or fragment thereof that binds a virion and reduces the infectivity of that virion. The ability of an antibody to neutralize a virus can be effectively tested, for example and without limitation, by a plaque assay as is broadly-known, e.g., in Cairns et al. 2017. In the context of the present invention, "major" neutralizing antibodies are neutralizing antibodies present in a majority of the population, such as in at least 10%, at least 20%, at least 30%, at least 40%, or at least 50% of a human population seropositive for HSV, e.g., HSV-1 or HSV-2, and selective for a specific epitope, e.g., epitopes described herein, and in Cairns et al. 2017 as MC5, MC23, DL11, MC14,1D3, and 11 B3AG, or as "red community", "pink community", or "blue community" epitopes, or in groups Ia, Ib, and III, as shown in Cairns et al. 2017 (reproduced in table 1, below) (see also, Cairns, T M, et al. (2015) Patient-Specific Neutralizing Antibody Responses to Herpes Simplex Virus Are Attributed to Epitopes on gD, gB, or Both and Can Be Type Specific. *J. Virology* 89(18):9213-9231 ("Cairns et al. 2015")). For gB, major epitopes include SS144, C226, and SS10, as indicated in Cairns et al. 2015 (see, also, Cairns et al. 2014. Mechanism of Neutralization of Herpes Simplex Virus by Antibodies Directed at the Fusion Domain of Glycoprotein B. *J. Virol.* 88(5):2677-2689; Bender F C, et al. 2007. Antigenic and mutational analyses of herpes simplex virus glycoprotein B reveal four functional regions. J Virol 81(8):3827-3841; Kousoulas, K G, et al., (1988) Antibody-resistant mutations in cross-reactive and type-specific epitopes of herpes simplex virus 1 glycoprotein B map in separate domains*Virology* 166(2): 423-431; Sanchez-Pescador, L, et al. (1993) Antibodies to Epitopes of Herpes Simplex Virus Type 1 Glycoprotein B (gB) in Human Sera: Analysis of Functional gB Epitopes Defined by Inhibition of Murine Monoclonal Antibodies *J. Infectious Diseases* 168(4):844-853; and Highlander, S L, et al. (1989) Identification of mar Mutations in Herpes Simplex Virus Type 1 Glycoprotein B Which Alter Antigenic Structure and Function in Virus Penetration J. Virol 63(2):730-738). Neutralizing antibodies may be classified with respect to their target epitope in a virion, such as an envelope glycoprotein, e.g., gD or gB. Major neutralizing antibodies bind to a corresponding "major epitope" in an envelope glycoprotein.

TABLE 1

Properties of anti-gD mAbs (Cairns et al. 2017).

| Group | mAb | gD binding | Epitope residues | Plaque Assay IgG (µg/mL) for 50% neutralization of: HSV-1 (KOS) | HSV-2 (333) |
|---|---|---|---|---|---|
| Ia | HD1 | TC | 216 | 4 +/− 1.4 | 4.7 +/− 1.8 |
|  | HD2 | TC | ND | 4 +/− 1.4 | 6.5 +/− 2.1 |
|  | LP2 | TC | 216 | 2.6 +/− 3.3 | 2.7 +/− 1.1 |
|  | MC23 | TC | 213, 216 | 1.6$^a$ | 0.26$^a$ |
|  | DL15* | TC | ND | 3.2 +/− 4 | NN |
| Ib | DL11 | TC | 36, 132, 140, 222-224 | 0.004$^a$ | 0.31$^a$ |
|  | 77S* | TC | 36, 222-224 | 0.1 +/− 0.1 | 1.4 +/− 1.6 |
|  | 97S* | TC | 36, 222-224 | 0.9 +/− 0.1 | 1.8 +/− 2.3 |
|  | 106S* | TC | 38, 222-224 | 2.3 +/− 1 | 2.1 +/− 1.9 |
|  | 108S* | TC | 38, 222-224 | 0.6 +/− 0.5 | 0.4 +/− 0.5 |

TABLE 1-continued

Properties of anti-gD mAbs (Cairns et al. 2017).

| Group | mAb | gD binding | Epitope residues | Plaque Assay IgG (µg/mL) for 50% neutralization of: HSV-1 (KOS) | HSV-2 (333) |
|---|---|---|---|---|---|
| IIa | MC4 | TC | 262-272 | NN$^a$ | NN$^a$ |
|  | MC8 | TC | 262-272 | NN$^a$ | NN$^a$ |
|  | MC9 | TC | 262-272 | NN$^a$ | NN$^a$ |
|  | MC10 | TC | 262-272 | NN$^a$ | NN$^a$ |
|  | MC14 | TC | 262-272 | NN$^a$ | NN$^a$ |
|  | MC15 | TC | 262-272 | NN$^a$ | NN$^a$ |
|  | BD78 | TC | 262-272 | 21 +/− 12.7 | 12 +/− 4.2 |
|  | BD80 | TC | 262-272 | 19 +/− 6.6 | 9 +/− 0 |
| IIb | DL6 | TC | 272-279 | NN$^a$ | NN$^a$ |
| IIc | 4E3E* | TC | ND | 2.3 +/− 2.4 | 5 +/− 5.6 |
|  | 4G4D* | TC | ND | 3 +/− 0 | 16.2 +/− 18 |
| III | VID | TC | 54 | 3$^b$ | 13$^b$ |
|  | 11S | TC | ND | 5.3 +/− 2.6 | NN |
|  | 3D5* | T1S | ND | 6.7 +/− 1.1 | NN |
|  | MC5 | TC | 75-79 | 3.1$^a$ | 6.2$^a$ |
|  | H162* | TC | ND | 20.7 +/− 27.2 | 7.3 +/− 5.1 |
|  | H193* | TC | ND | 21.7 +/− 25.8 | 39 +/− 93 |
| IV | 45S | T1S | ND | 21.3 +/− 17.2 | NN |
|  | D10-G12* | TC | ND | 2.5 +/− 1.9 | NN |
| VII | 110S | TC | 1-29 | 1.8 +/− 2.4 | 5 +/− 5.6 |
|  | 1D3 | TC | 10-20 | 0.39$^a$ | 6.2$^a$ |
|  | MC1 | TC | 10-20 | NN | NN |
|  | H170 | TC | 1-23 | 5.9 +/− 1.6 | 20.7 +/− 14.1 |
| X | HD3 | TC | ND | 4 +/− 0.7 | 22.5 +/− 10.6 |
| XII | AP7 | TC | 25, 27, 294 | 24.7 +/− 22.7 | NN |
|  | 12S* | TC | ND | 2.5 +/− 1.4 | NN |
| XVII | 11B3AG* | TC | ND | 0.9 +/− 0.6 | NN |
|  | A18* | T1S | 246 | 12.5 +/− 7.8 | NN |
|  | MG2 | T2S | 248 | NN$^a$ | 0.78$^a$ |

It should be recognized that the genome sequences of several HSV strains are known to persons of ordinary skill (e.g., MacDonald, J. Virol., 86(11): 6371 (2012); McGeoch, J. Gen. Virol., 69: 1531-1574 (1988); GenBank Accession No. J0673480; NCBI Reference Sequence: NC_001806.1; MacDonald, J. Virol. 86(17): 9540 (2012); GenBank Accession No. JX142173, which are incorporated herein by reference). Accordingly, manipulation of the sequence of HSV genes and loci is within the level of ordinary skill. It should also be noted that these published sequences, and the sequences provided herein (SEQ ID NOS: 1-4), are merely exemplary and that other strains or variants of HSV can be employed as a source genome in engineering the inventive virus particle or vector.

An HSV particle may be retargeted by disrupting, e.g. deleting or otherwise rendering ineffective, targeting of the virion to its normal binding targets, including nectin-1 (CD111/HveC), nectin-2 (CD112/HveB), HVEM (TNFRSF14/HveA), and 3-O-sulfated heparan sulfate (3-OS HS). Nectin-1 is the main receptor for HSV-1 and HSV2, nectin-2 is a receptor for HSV-2 and for certain mutant strains of HSV-1 (ANG, KOS-rid1, KOS-rid2) that have a mutation that blocks HVEM binding (e.g. Q27P). HVEM is mainly expressed on lymphocytes. 3-OS HS is a less well-defined receptor for HSV-1 gD only whose binding can be eliminated by mutations in the HVEM-binding region (Yoon et al, DOI: 10.1128/JVI.77.17.9221-9231.2003). In the case of gD of HSV-1, deletion of Y38, and replacement of the HVEM targeting moiety with a retargeting ligand sequence, such as an scFv, or another ligand, such as a single-domain (VHH) antibody, an affibody or a natural receptor binding partner sequence, such as a growth factor, as are broadly-known in the recombinant HSV field (see, e.g., U.S. Pat. No. 9,593,347 and Goins, W F, et al. *Curr Opin Virol.* 2016 December; 21: 93-101), can be used to alter the specific receptor dependence of HSV infection, i.e. retarget the virus.

As used herein, "modification" of an amino acid sequence, protein, epitope, antigenic determinant, etc. includes any mutation type that changes the amino acid sequence of a protein. In embodiments, the modifications are non-conservative in that they alter the binding of one or more antibodies to the protein. Suitable modifications include, without limitation: deletion of one or more amino acids, substitution of one or more stated amino acids (e.g., missense mutations), or insertion of one or more amino acids. Although specific amino acid substitutions are listed in the examples below (for HSV-1 gD (gD1), P54Q and T213M), substitution of the same amino acids, that is, amino acid residues P54 and/or T213 of gD1, with certain other amino acids may modify the relevant epitope, e.g. antibody binding, preferably without substantially disrupting infectivity of the virion for a target cell. Likewise, other amino acids associated with epitopes of HSV-1 gD (gD1 or HSV-2 gD (gD2)), such as amino acids 10-20, 75-79, 132, 140, 213, 216, 222-224, and 262-279 of SEQ ID NOS: 1 or 2 or amino acids corresponding to those amino acids, amino acids associated with major epitopes found in HSV-1 gB (gB1) or HSV-2 gB (gB2), such as, referencing SEQ ID NO: 3, amino acids 47 (e.g., N47T), 62 (e.g., A62T), 85 (e.g., G85D), 203 (e.g., A203T), 303 (e.g., Y303N), 304 (e.g., R304Q), 305 (e.g., E305K), 308 (e.g., H308Y), 328 (e.g., R328H), 335 (e.g., R335Q), 419 (D419K), 473 (e.g., S473N), 594 (e.g., G594R), 640-670, or, referencing SEQ ID NO: 4, amino acid 412 (e.g., E414K), or amino acids corresponding to those amino acids, and other amino acids in major epitopes of gD1, gD2, gB1, gB2, or retargeted versions thereof, corresponding to neutralizing antibodies, may be mutated to effectively modify the epitope in a manner consistent with the object of reducing neutralization, yet maintaining infectivity in a target cell. Further, determining the impact on antibody binding of any modification in any given epitope, and whether or not such modification can negatively impact infectivity in a target cell, is readily tested, such as in a plaque assay, western blotting or antibody binding assay, e.g. as described herein.

Many versions of HSV gD and gB that may find use, in original or modified form, in the virus particles described herein, are known to those of ordinary skill in the art. Those versions of gD and gB may have the wild-type (wt) sequence, e.g., as recited in SEQ ID NOS: 1-4, or variants thereof, including naturally-occurring or man-made variants thereof, or precursors thereof. Further, the numbering of the amino acids in HSV gD and gB glycoproteins may be presented differently, depending on the source of the sequence information. As such, where specific amino acids are referenced herein, they are in reference to amino acids in the context of SEQ ID NOS: 1-4. Unless specifically referring to the sequences of SEQ ID NOS: 1-4, modifications in amino acid sequences are therefore said to "correspond to" the referenced amino acids in SEQ ID NOS: 1-4, meaning the equivalent amino acids are modified in gD or gB glycoproteins that may vary in sequence or sequence numbering from the sequences of SEQ ID NOS: 1-4.

The present invention provides a recombinant HSV (rHSV), such as an oHSV, comprising a modified gB and/or a modified gD envelope glycoprotein in which one or more epitopes representing binding sites for one or more serum antibodies in HSV seropositive individuals are modified to reduce or eliminate neutralization of the recombinant HSV when administered to a patient seropositive for the one or more serum antibodies. That is, antibody binding of one or more major serum antibodies to gD or gB is reduced or eliminated. It is noted that mAbs are used as proxies for major serum antibodies in the examples.

By "recombinant", it is meant the viral genome is genetically modified or genetically engineered to encode amino acid changes, such as insertions, deletions, or substitutions, not present in the wild-type (wt) genome. As such, a protein sequence is considered to be "modified" if it has a sequence different from a wt (e.g., reference) sequence, such as one of SEQ ID NOS: 1-4. The rHSV may be derived from or engineered from HSV-1 acid/or HSV-2 genomes, including genomes of any suitable strain(s) or genetically-engineered version(s) of those genomes.

In practice, a recombinant HSV can be detargeted, and optionally retargeted. The recombinant HSV is detargeted or retargeted by removal of or destruction of the native cell-surface binding moieties in gD, e.g. the nectin-1 binding site by removal of, or substitution of Y38 (e.g., Δ38), and the HVEM binding sequence by removal or destruction, and optionally replacing the HVEM binding sequence with a ligand for binding a cell surface binding partner present on a target cell, such as an scFv sequence, for example and without limitation encoding an anti-EGFR/EGFRvIII scFv (see, e.g. FIG. 2), for targeting human glioblastoma cells, and other cancer cells. Optionally a cell-targeting ligand may be expressed as a separate protein or part of an envelope glycoprotein other than gD, such as in gB or gH (see, e.g., Petrovic, B, et al. Dual Ligand Insertion in gB and gD of Oncolytic Herpes Simplex Viruses for Retargeting to a Producer Vero Cell Line and to Cancer Cells. *J. Virology* February 2018, 92 (6) e02122-17; Petrovic B, et al. (2017) Insertion of a ligand to HER2 in gB retargets HSV tropism and obviates the need for activation of the other entry glycoproteins. *PLoS Pathog* 13(4): e1006352; and Gatta V, et al. (2015) The Engineering of a Novel Ligand in gH Confers to HSV an Expanded Tropism Independent of gD Activation by Its Receptors. *PLOS Pathogens* 11(5): e1 004907). Thus, by "retargeted", it is meant that a virus, e.g. an HSV virus is genetically or synthetically altered such that an envelope glycoprotein is modified to eliminate recognition of the normal virus cognate receptors (referred to as "detargeting"), and provided with a ligand, or mutation, to enable virus attachment and entry through recognition of a cell surface structure other than the normal virus cognate receptors.

The viral genome also may comprise one or more microRNA target sequences to reduce or prevent off-target infection and replication of the viral genome. Also provided herein are virus stocks and pharmaceutical compositions comprising the described rHSV, as well as methods for killing tumor cells employing the described rHSV (oHSV).

As described above, the HSV particle may comprise a non-HSV ligand specific for a molecule (protein, lipid, or carbohydrate determinant) present on the surface of a cell (such as a cancer cell) and/or one or more copies of one or more microRNA target sequences inserted into one or more HSV gene loci, such as one or more HSV gene(s) required for replication of HSV in normal cells.

The non-HSV ligand of the recombinant HSV (rHSV) is incorporated into a glycoprotein exposed on the HSV surface, such as gD or gC, to facilitate targeting the desired cell with the ligand. For example, the ligand can be incorporated between residues 1 and 25, between residues 24 and 25, or between residues 7 and 39 of gD. Ligands for targeting cancer cells, such as glioblastoma or breast cancer, include those targeting EGFR and EGFRvIII, HER2 (human epidermal growth factor receptor 2), CD133, CXCR4 (chemokine receptor type 4, fusin), carcinoembryonic antigen (CEA), CLC-3/annexin-2/MMP-2 (chlorotoxin receptor), human transferrin receptor, epithelial cellular adhesion molecule (EpCAM), or c-Met, and the ligand can target such a receptor or cell-surface molecule, i.e., the ligand is capable of specifically binding such receptor or cell-surface molecule. EGFR- and EGFRvIII-specific ligands, such as antibodies, scFvs (single chain antibodies) and VHHs (single domain antibodies), have been described in the literature (Kuan et al, *Int J. Cancer*, 88, 962-69 (2000); Wickstrand et al., *Cancer Res.*, 55(14):3140-8 (1995); Omidfar et al., *Tumor Biology* 25:296-305 (2004); see also Uchida et al, *Molecular Therapy*, 21:561-9 (2013); see also Braidwood et al., *Gene Ther.*, 15, 1579-92 (2008)).

The rHSV also or alternatively can be targeted by incorporating ligands to other cell-surface molecules or receptors that are not necessarily cancer-associated. For example, ligands can include binding domains from natural ligands (e.g., growth factors (such as EGF, which can target EGFR, NGF, which can target trkA, GDNF, which can target GFRα1, and the like)), peptide or non-peptide hormones, peptides selected for binding a target molecule (e.g., DARPins and affibodies), etc. The rHSV also can include a mutant form of gB and/or gH that facilitates virus entry though non-canonical receptors (and would typically also have such mutations in one or both of these genes within the rHSV genome).

An exemplary microRNA target sequence for inclusion in the rHSV vector (for example as multiple copies thereof in tandem) is a binding sequence for miR-124, which has particular application for neural applications (e.g., to protect non-cancerous neurons when employing the rHSV for treating nervous-system tumors, such as GBM). Other microRNA target sequences can alternatively be employed for protecting other types of tissues, and it is within the ordinary skill in the art to select a suitable microRNA target sequence to protect a desired tissue or cell type. For example, miR-122 and miR-199 are expressed in normal liver cells but not primary liver cancer; thus one, or a combination of miR-122 and/or miR-199 microRNA target sequences can be employed in an embodiment of the rHSV for treatment of liver cancers. Similarly, target sequences for miR-128 and/or miR-137 microRNA can be employed in oHSV for protection of normal brain. An exemplary microRNA target sequence can be the reverse complement of the microRNA. Where the rHSV is administered systemically, one or more microRNA target sequences are employed to protect non-target cells throughout the body.

The microRNA target sequence(s) may be included in the 3' untranslated region ("UTR") of an HSV gene, to silence that gene in the presence of the microRNA. It may be preferred that multiple copies (such as two copies, three copies, four copies, five copies, six copies, or more) of the microRNA target sequence are inserted in tandem. The multiple copies of the micro-RNA target sequence may be separated by spacers of four or more nucleotides (more preferably eight or more nucleotides). Multiple copies of the microRNA target sequences may be the same or different, such that target sequences of two or more microRNAs are presented in a single gene.

In embodiments of the rHSV, to assist in protecting non-cancerous cells from the lytic effect of HSV infection, multiple copies of one or more microRNA target sequence are inserted in the 3' UTR of an HSV gene that is essential for replication in non-cancerous cells, which are known to persons of ordinary skill. In examples, the site is the 3' UTR of the microRNA-targeted gene in its normal (or native) locus within the HSV genome. In one embodiment, a plurality of microRNA target sequences are inserted into the 3' UTR of the ICP4 gene, such as both copies of the ICP4 gene, in vectors which have both native copies of the ICP4 gene.

The genome of the rHSV vector additionally can comprise one or more exogenous expression cassettes containing encoding sequences, e.g., an open-reading frame (ORF), in operable linkage with promoters, enhancers, and other suitable regulatory elements for expression of the ORF. The encoding sequences, e.g., ORF, encode a gene product such as a protein, such as a reporter protein (such as green fluorescent protein), an oncolytic factor or agent that enhances tumor killing activity (such as tumor necrosis factor ("TNF") or TNF-related apoptosis-inducing ligand ("TRAIL"), or other therapeutically-important gene product (e.g., peptides, drug-activating enzymes, antibodies, therapeutic or regulatory RNAs, and the like).

Exemplary exogenous expression cassettes encode proteins or polypeptides that induce patient immune responses against the cancer or tumor to which the inventive HSV is to be employed to treat. For example, such expression cassettes can include one or more nucleic acids encoding factors such as cytokines (e.g., IL-12 and IFN-β), an antibody directed against cytotoxic T-lymphocyte-associated protein 4 ("CTLA-4") (Hodi et al., *N. Engl. J. Med.,* 363(8): 711-23 (2010)), an antibody directed against either the ligand of programmed cell death protein 1 ("PD1") or the receptor itself (Topalian et al., *N. Engl. J. Med.,* 366(26): 2443-54 (2012)), or epithelial cell adhesion molecule ("Ep-CAM") (Patriarca et al., *Cancer Treatment Rev,* 38: 68-75 (2012)). EpCAM can serve both as cellular target and rHSV targeting ligand. In one embodiment, an exogenous expression cassette encodes granulocyte-macrophage colony-stimulating factor ("GM-CSF"). The cassette can also encode proteins for "rewiring of aberrant signaling to effector release" (RASER), e.g., as described in Chung, H K, et al, (2019). A compact synthetic pathway rewires cancer signaling to therapeutic effector release. *Science* 364(6439), eaat6982, DOI: 10,1126/science.aat6982.

Other expression cassettes encode proteins or polypeptides that catalyze the conversion of prodrugs to active agents. For example, such expression cassettes can encode enzymes such as cytosine deaminase, which can convert 5-fluorocytosine ("5-FC") into 5-fluorouracil ("5-FU") locally in tumors or cancerous cells infected with the inventive vector (see, e.g., Akimoto et al., *J. Ophthalmol.,* 86(5): 581-86 (2002)), so as to permit 5-FU to act locally within such cells or tumors while minimizing systemic exposure to 5-FU. Similarly, such an expression cassette can encode thymidine kinase (tk) (e.g., operably linked to an HSV immediate-early promoter or strong constitutive, promoter), which can activate ganciclovir, or purine nucleoside phosphorylase (PNP), which can block or attenuate the activity of ribonucleotide reductase. In certain embodiments, the inventive vectors also can contain a functional native HSV tk gene.

Within the rHSV vector described herein, the encoding sequences within the exogenous expression cassettes can be in operable linkage with any desired genetic regulatory sequence, such as constitutive promoters or inducible or tissue-specific promoters, many examples of which are known in the art, or microRNA target sites. For example, a commonly-employed constitutive promoter is the human cytomegalovirus (hCMV) promoter, and other promoters also can be used, e.g., the CMV early enhancer/chicken beta actin (CAG) promoter, the HSV immediate early promoter (e.g., ICP4 promoter), and the like.

Also, in certain embodiments, the genome of the inventive vector contains a deletion of the internal repeat (joint) region comprising one copy each of the diploid genes ICP0, ICP34.5, LAT and ICP4 along with the promoter for the ICP47 or ICP22 gene. In other embodiments, instead of deleting the joint, the expression of genes in or flanking the joint region, particularly ICP0, ICP34.5, and/or ICP47, can be silenced by deleting these genes or otherwise subjecting them to limited mutagenesis impeding their expression or product functionality.

The rHSV vector can be produced by standard methods known to persons of ordinary skill in the field of HSV virology. However, to facilitate manipulation of the HSV genome and production of the inventive vector, the invention also provides a nucleic acid representing the inventive vector genome. In one aspect, the nucleic add is a bacterial artificial chromosome ("BAC") encoding the rHSV vector, which facilitates manipulation of the HSV in a bacterial system.

The rHSV described herein can be used to target and kW cancerous cells, whether in vivo or in vitro. In one application, the rHSV vector is employed therapeutically, e.g., in human patients and/or against human tumors/cells (which can be xenografts in various mammalian species). However, the method also may be employed in animals, such as companion animals (e.g., cats and dogs), or animals of agricultural importance (e.g., cattle, sheep, horses, and the like), or of zoological importance. Exemplary tumors/cancerous cells, the treatment of which the inventive vectors can be employed for, include: cancers of the central nervous system, such as glioblastoma multiforme (e.g., EFGR/vIII-targeted), breast cancers (e.g., HER2-targeted), squamous cell carcinoma of the head and neck (HNSCC, e.g., EFGR/vIII-targeted), prostate cancers (e.g., EFGR/vIII-targeted), and lung cancers (NSCLC) (e.g., EFGR/vIII-targeted).

Generally, the rHSV vector is most useful when enough of the virus can be delivered to a cell population to ensure that the cells are confronted with a suitable number of virus particles. Thus, the present invention provides a stock, e.g. a homogeneous stock, comprising the rHSV vector. The preparation and analysis of HSV stocks is well known in the art. For example, a viral stock can be manufactured in roller bottles or multi-layer cell stacks containing cells transduced with the rHSV vector. The viral stock can then be purified on a continuous density gradient medium, such as a NYCODENZ® gradient, and aliquotted and stored until needed. Viral stocks vary considerably in titer, depending largely on viral genotype and the protocol and cell lines used to prepare them. It may be preferred that such a stock has a viral titer of at least about $10^5$ plaque-forming units (pfu), such as at least about $10^6$ pfu, at least about $10^7$ pfu, at least about $10^8$ pfu, at least about $10^9$ pfu, at least about $10^{10}$ pfu, or at least about $10^{11}$ pfu.

The invention additionally provides a composition comprising the inventive oHSV vector and a carrier, preferably a physiologically-acceptable or pharmaceutically-acceptable carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well-known and are readily-available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition may comprise additional therapeutic or biologically-active agents, or the additional therapeutic or biologically-active agents may be co-administered with the rHSV. For example, therapeutic factors useful in the treatment of a particular indication can be present or co-administered. Factors that control inflammation, such as ibuprofen or steroids, can be part of the composition or co-administered to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition or co-administered to upregulate the body's natural defenses against disease, particularly against the cancer or tumor against which the inventive vector is to be used. Antibiotics, e.g., microbicides and/or fungicides, can be included in the composition or co-administered to reduce the risk of infection associated with gene transfer procedures and other disorders.

Figure 7A:
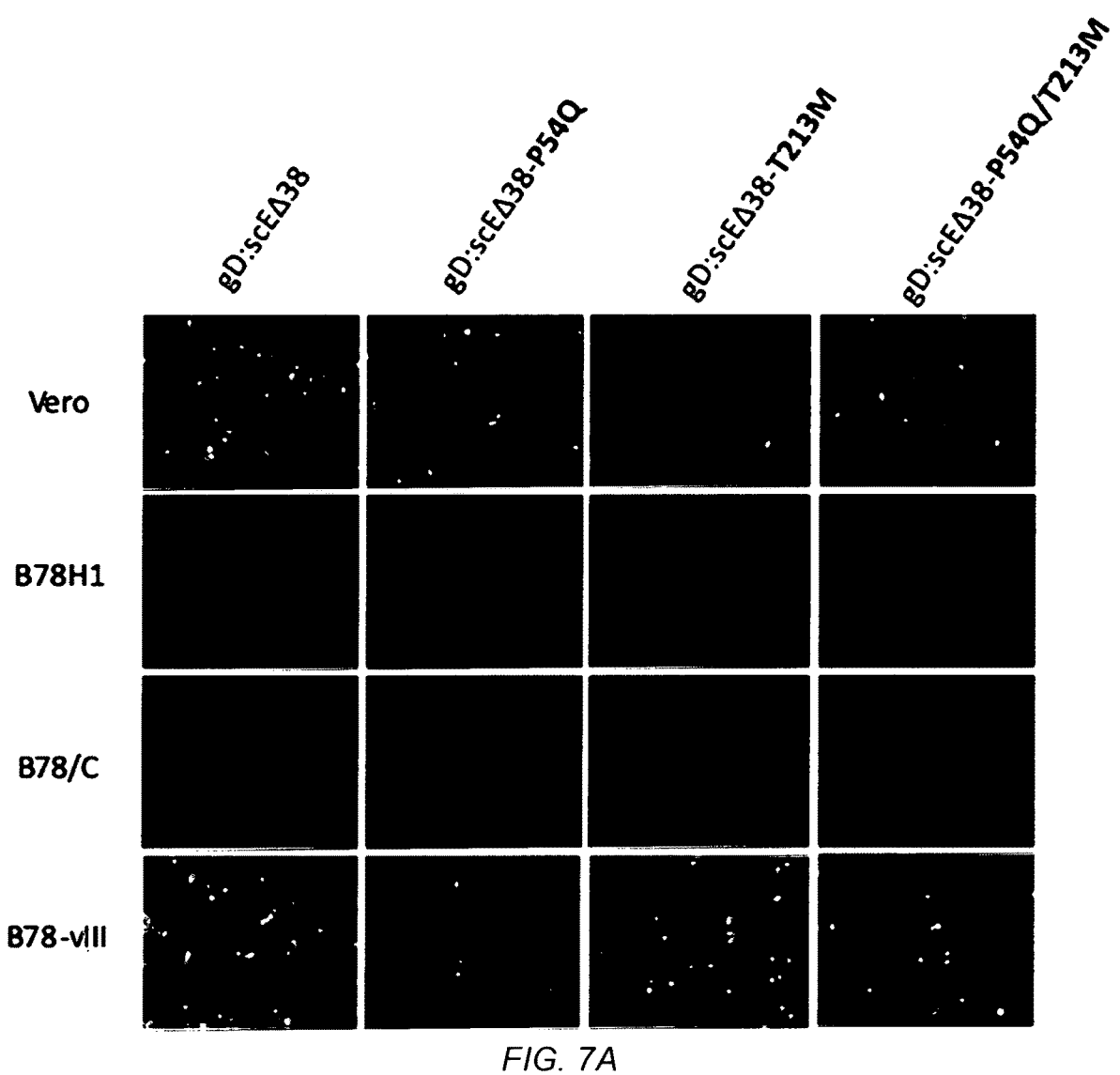
FIGS. 7A and 7B. Virus entry specificities and virion incorporation of gD.
Figure 7B:
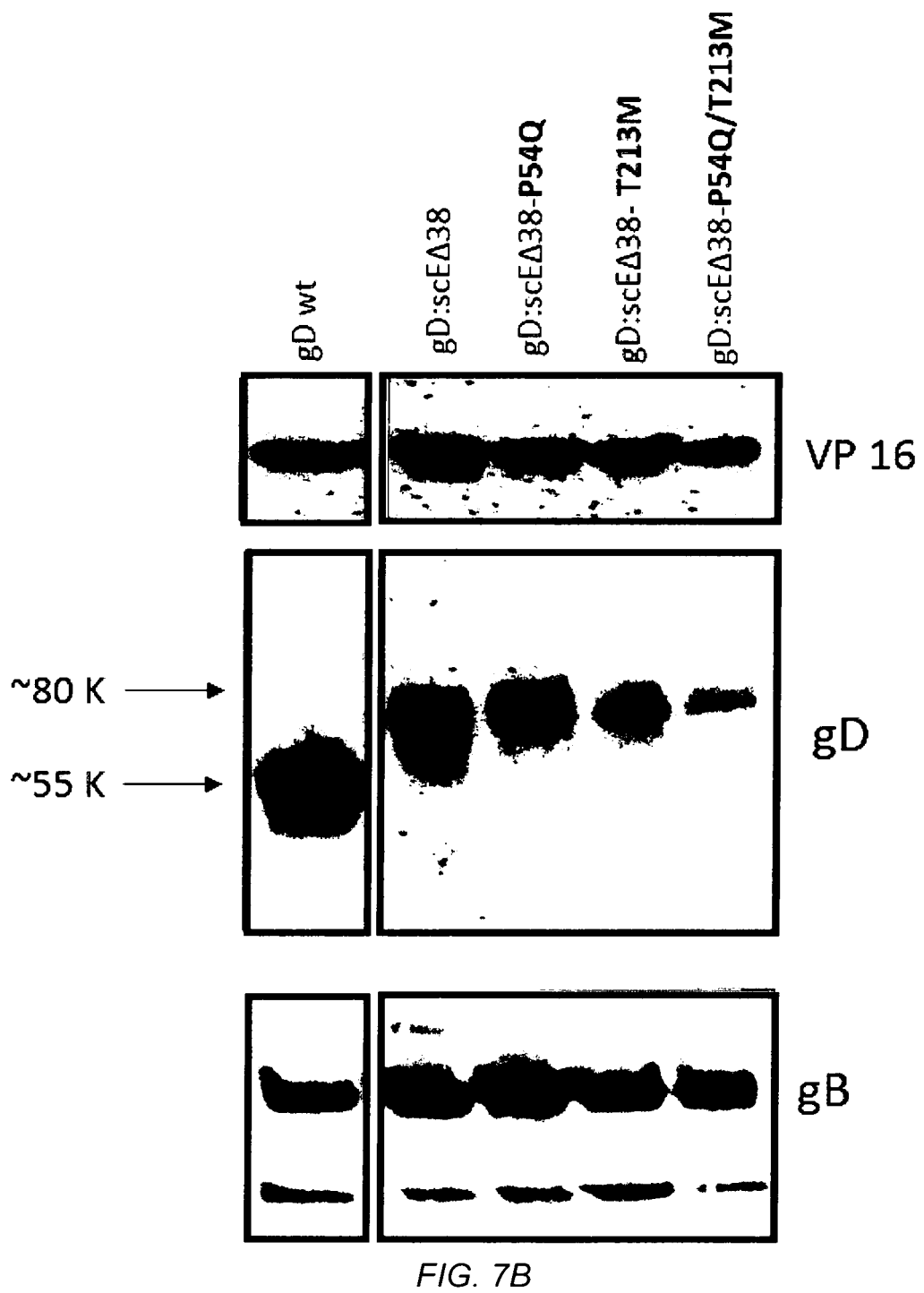

A retargeted rHSV was prepared as depicted in FIG. 3. The HSV-1 genome consists of two unique regions (unique long [UL], 108 kb, and unique short [US], 13 kb), each flanked by large inverted repeats. A recombination cassette (GW) was inserted in place of the gD coding sequence (ΔgD:GW) to allow rapid, orientation-specific insertion of altered gD genes under control of the gD promoter. This backbone contains bacterial artificial chromosome (BAC) sequences that allow generation of mutant viral genomes in bacteria and production of infectious viruses by transfection of suitable mammalian cell lines. The construct further contains a ubiquitin C promoter (UbCp) driven mCherry reporter gene to observe retargeted virus entry and a viral entry-enhancing mutant gB gene (gB:NT or gB:N/T; Uchida et al, A Double Mutation in Glycoprotein gB Compensates for Ineffective gD-Dependent Initiation of Herpes Simplex Virus Type 1 Infection. J Virol 2010: 12200-12209. DOI: 10.1128/JVI.01633-10; Uchida et al, Effective treatment of an orthotopic xenograft model of human glioblastoma using an EGFR-retargeted oncolytic herpes simplex virus. Mol Ther 21, 561-569, doi:10.1038/mt.2012.211 (2013)). gD wt includes the wild-type gD sequence from strain KOS, including the signal peptide (residues −25 to −1), HVEM binding site, nectin-1 binding site (including Y38), the transmembrane region (TM), and the cytoplasmic tail region (CT). The open reading frame of gD:scEΔ38 deletes residue Y38, disrupting the nectin-1 binding site, and replaces residues 2-24 of the HVEM binding site with anti-EGFR/EGFRvIII scFv sequence—effectively retargeting the rHSV (FIGS. 7A and 7B).

EXAMPLES

Approximately 70% of the human population is HSV seropositive, Therefore, we asked whether changing the epitope structure of retargeted gD by mutagenesis of epitopes recognized by HSV-neutralizing anti-gD antibodies would reduce retargeted gD and retargeted virus recognition by monoclonal, and possibly polyclonal, anti-gD antibodies to increase virus resistance to virus-neutralizing (VN) sera. We compared the binding of a panel of monoclonal antibodies (mAbs) that mimic antibody specificities in human HSV-immune sera to the purified ectodomains of wild-type and retargeted gD, revealing the retention of two prominent wild-type gD epitopes in retargeted gD. Substitution of a key residue in each epitope, separately and together, led to the following observations: Both substitutions (i) blocked retargeted gD recognition by mAbs to the respective epitopes, and in combination, caused a global reduction in mAb binding; (ii) protected against fusion inhibition by VN mAbs reactive with each epitope in virus-free cell-cell fusion assays; and (iii) increased the resistance of retargeted HSV-1 to these VN mAbs. Mutagenesis to eliminate additional shared epitopes is expected to further decrease retargeted virus susceptibility to neutralizing antibodies.

Materials and Methods:
Plasmids pENTR-based plasmids for viral genome modification: The complete gD wt and gD:scEΔ38 coding sequences (e.g., encoding SEQ ID NO: 1) were cloned between the Gateway (GW)-compatible attL sites of plasmid pENTR1A. The P54Q substitution was generated by introducing an internal BstBI site, to insert a synthetic DNA fragment (GenScript) specifying the codon 54 change from CCG to CAG flanked by BstBI and BspEI sites. Likewise, the T213M substitution was introduced by replacement of a synthetic DNA fragment (GenScript) specifying the codon T213M change from ACG to ATG with the use of KasI and FspI sites.

pVT-Bac-based plasmids for gD ectodomain expression and purification: The coding sequences for the mature ectodomains (residues 1-306) of wt, retargeted and mutant retargeted gDs were isolated by PCR amplification with primers pVT Bac gD:scEGFR Δ38 5', CCAGCCCGGGCAAAGACATTCTAATGACC-CAATCTC (SEQ ID NO: 7), introducing a SmaI site (underlined); and pVT Bac gD:scEGFR Δ38 3' GGTATGCGGCCGCT-TAATGGTAAGGCGTCGCGGCGTCCT (SEQ ID NO: 8), introducing a NotI site (underlined). Respective pENTR recombinants were used as templates and the PCR products were cloned into baculovirus expression plasmid pVT-Bac to produce soluble proteins.

pcDNA3.1-based plasmids for gD expression in mammalian cells: The coding sequences for wt and retargeted gDs were cloned into a modified pcDNA 3.1 plasmid that contains a Gateway (GW) recombination cassette between the CMV promoter and bovine growth hormone (bGH) polyadenylation region (pcDNA-GW; Reinhart et al., An HSV-based library screen identifies PP1α as a negative TRPV1 regulator with analgesic activity in models of pain, Mol Ther 2016, 3:16040, doi:10.1038/mtm.2016.40) by LR Clonase II (ThermoFisher, Waltham, MA)-mediated recombination with the respective pENTR-based plasmids.

Other plasmids: gB:NT expression plasmid pCAgB:NT was as described in Uchida, H., et al., Novel mutations in gB and gH circumvent the requirement for known gD Receptors in herpes simplex virus 1 entry and cell-to-cell spread. J Virol, 2013. 87(3):p. 1430-42. gH and gL expression plasmids pPEP100 and pPEP101, respectively, were kindly provided by Patricia Spear (Northwestern University). PT3.5/CMV-EGFRvIII, made available by John Ohlfest (University of Minnesota), was purchased from Addgene (plasmid #20280). pCX4-bsr-DEST, pCL-gag-pol and pHCMV-VSVG were kind gifts from Akihiro Umezawa (NRICHD, Tokyo, Japan). pCX4-bsr-EGFRvIII was constructed by PCR amplification of the EGFRvIII coding sequence from plasmid PT3.5/CMV-EGFRvIII (Weisner, S M, et al. De novo induction of genetically engineered brain tumors in mice using plasmid DNA. Cancer Res. 2009 Jan. 15; 69(2):431-9. doi: 10.1158/0008-5472.CAN-08-1800) with primers Sal1EGFRvIIIF (gactagtcgacAAT-TCGTTGGCCGCATGCGA, SEQ ID NO: 9) and Xho1EGFRvIIIR (cactactcgagTCATGCTCCAATAAATT-CACTGCTTTG, SEQ ID NO: 10). The PCR fragment was transferred into pENTR1a (ThermoFisher) by SalI-XhoI enzyme digestion and cloning between the SalI and XhoI sites of pENTR1a. The EGFRvIII coding sequence was transferred from pENTR1a to pCX4-bsr-DEST by LR Clonase II-mediated recombination. All new constructs were confirmed by DNA sequencing.

Viruses A GW-compatible gD-null viral backbone, KNTc-ΔgD:GW (FIG. 3), on a bacterial artificial chromosome (BAC) was derived from KNTc BAC (Miyagawa, Y., et al., Herpes simplex viral-vector design for efficient transduction of nonneuronal cells without cytotoxicity. Proc Natl Acad Sci USA, 2015. 112(13): p. E1632-41) by Red-mediated replacement of the gD coding sequence with a GW cassette, GW-Zeo, amplified with primers targeting the proximal 5' and 3' gD untranslated sequences, essentially as described in Miyagawa et al. Wt and retargeted gD genes were then introduced by LR Clonase II-mediated recombination of the GW cassette with the different pENTR-based gD plasmids. Infectious viruses were produced by transfection of Vero cells and biological titers were determined by standard plaque assays on Vero cells. All recombinant viruses were confirmed by DNA sequencing across the gD cassettes.

Figure 4:
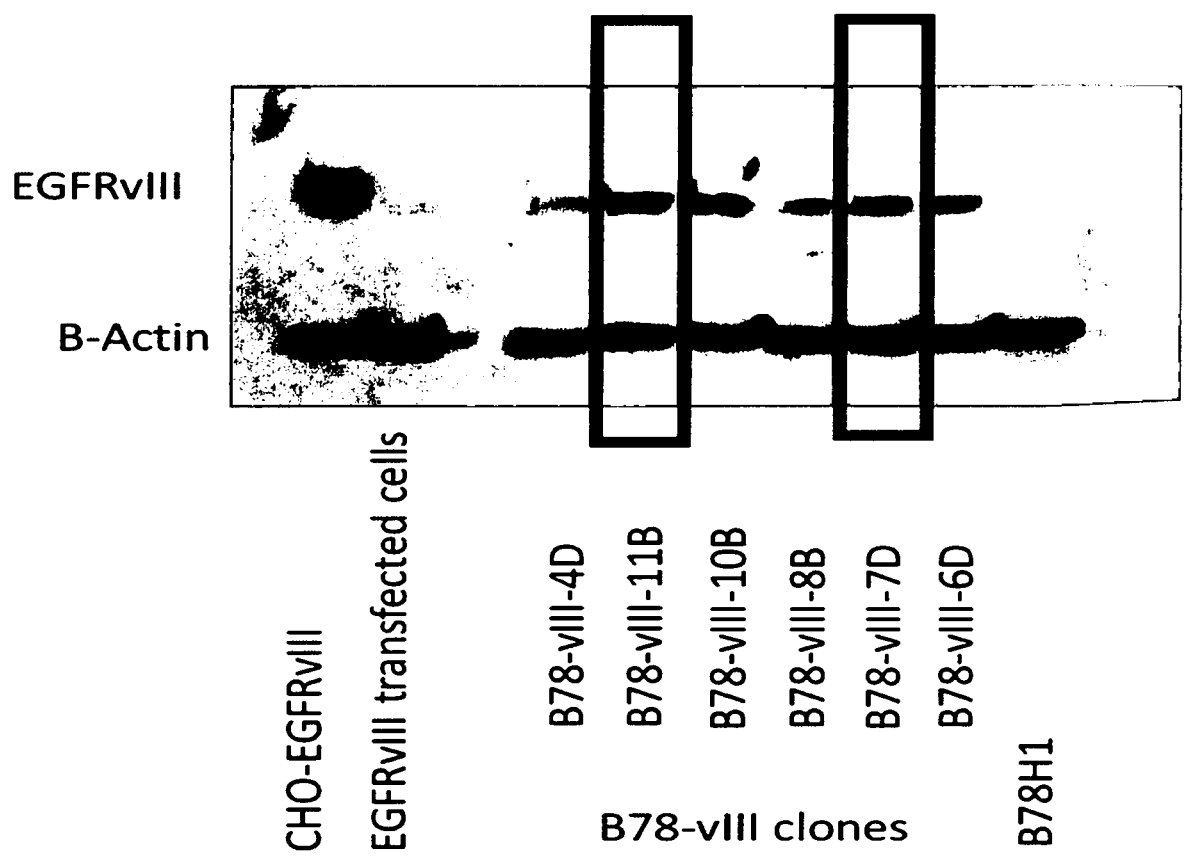
FIG. 4 shows the generation and characterization of B78-EGFRvIII clones (B78-vIII). B78-H1 mouse melanoma cells were infected with an EGFRvIII-expressing recombinant retrovirus. Transduced cells were selected for resistance to 10 μg/ml blasticidin, pooled and sorted by EGFRvIII expression level using anti-EGFR monoclonal antibody H11 and a fluorescence activated cell sorter (FACS). Cells from the front and back of the EGFRvIII-positive peak were separately cloned by limiting dilution and individual clones were analyzed by Western blot (WB) for EGFRvIII expression. Results show EGFRvIII expression in selected B78-vIII clones. Chinese Hamster Ovary (CHO-K1) cells expressing EGFRvIII (CHO-EGFRvIII) were used as the positive control. B78H1 cells were negative for EGFRvIII (B78H1, far right). B78H1 cells transiently transfected with an EGFRvIII expression plasmid exhibited barely detectable expression of EGFRvIII. β-Actin was visualized as a loading control. B78-vIII clone 11B was chosen for subsequent experimental studies.

Cells Murine melanoma B78H1, B78-C10 (nectin-1-transduced B78H1; Miller, C. G., et al., Development of a Syngenic Murine B16 Cell Line-Derived Melanoma Susceptible to Destruction by Neuroattenuated HSV-1, MolTher 2001, 3:160-168, doi:10.1006/mthe.2000.0240) and B78/C cells (nectin-1-transduced B78H1) (Uchida, H., et al., Generation of herpesvirus entry mediator (HVEM)-restricted herpes simplex virus type 1 mutant viruses: resistance of HVEM-expressing cells and identification of mutations that rescue nectin-1 recognition. J Virol, 2009. 83(7): p. 2951-61) were cultured in Dulbecco's modified Eagle's medium (DMEM; Invitrogen, Carlsbad, CA) supplemented with 5% fetal bovine serum (FBS; Invitrogen). African green monkey kidney Vero cells (ATCC CCL-81) were cultured in DMEM supplemented with 5% FBS. B78-vIII cells were established by infection of B78H1 cells with a recombinant retrovirus expressing EGFRvIII, produced by co-transfection of 293T cells (ATCC CRL-3216) with plasmids pCX4-bsr-EGFRvIII, pCL-gag-pol and pHCMV-VSVG. Infected B78H1 cultures were selected for resistance to blasticidin and resistant pools were tested for EGFRvIII expression by Western blots and flow cytometry analysis with anti-EGFR mAb H11 (ThermoFisher). After validation, the cells were sorted at the Cell Sorting Facility of the University of Pittsburgh McGowan Institute based on expression levels and clones denoted B78-vIII were isolated from a high-expressing fraction by limiting dilution. EGFRvIII expression by different B78-vIII clones is shown in FIG. 4. One clone (11 B) was used in the current study.

gD Ectodomain Production and mAb Binding (SPRi) Assays. All soluble proteins used were produced in baculovirus-infected insect (Sf9) cells. All variants of HSV-1 gD(306t) were purified using a DL6 immunosorbent column as described in Sisk W P, Bradley J D, Leipold R J, et al. (High-level expression and purification of secreted forms of herpes simplex virus type 1 glycoprotein gD synthesized by baculovirus-infected insect cells. J Virol. 1994;68(2):766-775). Analysis of gD-mAb binding was performed using soluble proteins on the Wasatch Microfluidics CFM/SPRi system as described in Cairns T M, Ditto N T, Lou H, et al. (Global sensing of the antigenic structure of herpes simplex virus gD using high-throughput array-based SPR imaging. PLoS Pathog. 2017;13(6):e1006430). A CFM 2 was used to create a 48-spot microarray of amine-coupled mAbs on a CDM200M sensor chip (Xantec GmbH). Upon docking the printer chip into the SPR imager (IBIS MX96), the chip was blocked with ethanolamine and the system primed with a running buffer of PBS-0.01% Tween 20. mAb binding was assessed by flowing 100 nM soluble gD across the printed mAb array; 1M glycine pH 2.0 was used for regeneration.

Fusion Assay. The fusion assay is described in Atanasiu D et al., (Dual split protein-based fusion assay reveals that mutations to herpes simplex virus (HSV) glycoprotein gB alter the kinetics of cell-cell fusion induced by HSV entry glycoproteins. J Virol. 2013;87(21):11332-11345) and Saw et al., (Using a split luciferase assay (SLA) to measure the kinetics of cell-cell fusion mediated by herpes simplex virus glycoproteins. Methods. 2015;90:68-75.) Briefly, $5\times10^4$ B78H1 cells (effector cells) were seeded on white, cell-culture treated 96-well plates. $4\times10^5$ B78-vIII cells (target cells) were seeded on 6-well plates. Transfection was performed the following day. A master mix containing 375 ng gB:NT, 125 ng each of the indicated gD construct, wt gH, wt gL, and $Rluc8_{(1-7)}$ was split over three wells of effector cells. Target cells were transfected with 1 µg of $Rluc8_{(8-11)}$ plasmid/per well. Forty-eight hours post-transfection effector cells were pre-incubated for 1 h at 37° C. with EnduRen substrate (Promega) diluted in fusion medium (DMEM without phenol red, 50 mM HEPES and 5% FBS). Target cells were detached with versene, resuspended in fusion medium and transferred to effector cells. Fusion was triggered by the addition of target cells. A negative control (effector cells transfected with gB:NT, gH, gL, but no gD) was also included. Luciferase production was monitored over 6 h with measurements every hour using a BioTek plate reader.

Blocking of fusion. Transfected effector cells were pre-incubated with both EnduRen substrate and serial, 2-fold dilutions of the indicated gD mAbs beginning at 20 µg/ml mAbs, based on 80 µl final volumes.

Entry Assay. Cells were infected overnight at MOI=1 and imaged for mCherry expression under a Nikon Diaphot fluorescence microscope (Nikon, Melville, NY).

Real-Time PCR. Viral DNA was isolated using the Blood and Tissue DNA Extraction Kit (Qiagen, Venlo, Netherlands). Genome copy (gc) titers were then determined by creating a standard curve with an HSV-1 UL5 plasmid DNA template. The UL5 DNA sequence was amplified by PCR with primers ULSF (ACGAGCGTGGTGCGGTCATGG) (SEQ ID NO: 11) and ULSR (GCGGGTTAATA-GACAATGACCACG) (SEQ ID NO: 12), and cloned into the pCR-Blunt II-TOPO vector using the Zero Blunt TOPO PCR cloning kit (ThermoFisher). A custom FAM-MGB Taqman primer probe set (ThermoFisher) was designed against the UL5 gene (UL5 qPCR F primer ATGCCGTAGTCGGCGTTTAT (SEQ ID NO: 13); UL5 qPCR R primer CGAGTTTGTCGAGTCCATTGAC (SEQ ID NO: 14); UL5 FAM MGB probe ATGGCCAGCTCCGTAG (SEQ ID NO: 15)). Standard curves were generated for each experiment by creating a 10-fold dilution series of the UL5 plasmid (representing $3\times10^6$ gc corresponding to $3\times10^2$ gc of the HSV genome) that was amplified with an efficiency of 98-100%. Reaction conditions: 2 µl DNA, 1 µl of the 20× UL5 FAM-MGB Taqman primer probe set, 10 µl TaqMan Fast Advanced Universal PCR Master Mix (2×) in a total PCR volume of 20 µl. Amplification conditions: 2 min at 50° C. and 20 sec at 95° C. for the first cycle, followed by 40 cycles of 95° C. for 1 sec and 60° C. for 20 sec. Samples, standard curve, and negative controls were run together in triplicate in Micro-Amp Optical 96-Well Reaction Plates with the StepOne Plus Real Time PCR system (Applied Biosystems).

Western Blots. Equal gc-based amounts of purified virus stocks were denatured by boiling in 1× Laemmli buffer (Bio-Rad Laboratories, Hercules, CA) and electrophoresed on precast 4-15% SDS-PAGE gels (Bio-Rad Laboratories). Proteins were transferred to PVDF membranes (Millipore, Billerica, MA) and horizonally-cut portions of the membranes were reacted with anti-VP16 (Santa Cruz, Dallas, TX), anti-gD (DL6, Santa Cruz, Dallas, TX) or anti-gB (Virusys Corp., Taneytown, MD) prior to incubation with HRP-conjugated rabbit anti-mouse IgG (Abcam, Cambridge, UK). Membranes were developed with ECL Plus (ThermoFisher).

Virus Neutralization Recombinant viruses (50-75 PFU/well) were incubated with virus-neutralizing mAbs MC5 and MC23 at a range of dilutions prior to infection of Vero cells. Infected cell monolayers were overlayed with high-density medium and plaques were counted 48 h later under the Nikon Diaphot fluorescence microscope.

Results

Retargeting Induces Changes in the Antigenic Structure of gD.

We used SPRi analyses of purified gD ectodomains to compare the epitope landscapes of wt and retargeted gD. No binding to retargeted gD was observed for any of the yellow group mAbs (FIG. 5(A)). This was expected since these mAbs (Group VII in Table 1) recognize the HVEM binding N-terminal segment of wt gD (Table 1) that is largely replaced with our anti-EGFR/EGFRvIII scFv in the retargeted gD. In addition, we observed decreased binding to green community mAbs as well as to tan mAbs (VN members of the brown group), with some reduction among mAbs from the red and blue groups. Interestingly, all non-VN mAbs in the brown group showed increased binding (See, Cairns et al. 2017, and above, describing the various colored groups or "communities").These observations indicated that the retargeting modifications broadly affect the conformation of gD.

mar Mutations Further Change the Antigenic Structure of Retargeted gD and Reduce the Binding of Specific Neutralizing mAbs To eliminate the binding of neutralizing mAbs, we created substitution mutations P54Q and T213M in retargeted gD. Based on SPRi results, P54Q (FIG. 5(B)) completely abolished the binding of MC5 and another blue mAb, H162, that had shown increased binding to parental retargeted gD (FIG. 5(A)). This mutation also decreased the binding of two other blue mAbs as well as of the green, brown and tan mAbs, but less dramatically (FIG. 5(B)). T213M appeared to have a more specific effect, causing mildly to severely impaired binding of the red group of mAbs, MC23 in particular, but no major changes in the binding of other mAbs (FIG. 5 (C)). Combining the two mutations in retargeted gD (P54Q/T213M) suggested an additive effect, closely resembling the binding profile of P54Q alone but with limited binding of red mAbs (FIG. 5(D)). Collectively, these results indicated that stacking of rational substitution mutations can broadly reduce the antigenic composition of retargeted gD.

mar Mutations Reduce the Virus-Free Cell-Cell Fusion Activity of Retargeted gD

Figure 6A:
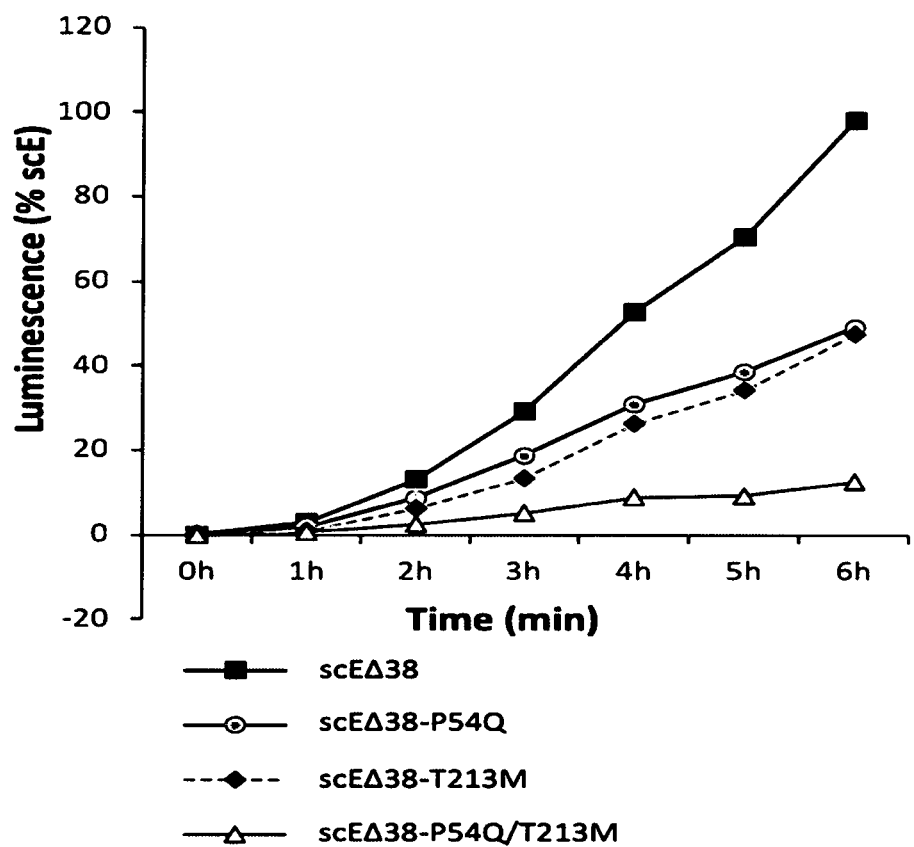
FIGS. 6A-6C. gD activity in virus-free fusion assays and inhibition by mAbs. To measure gD fusion activity, an effector cell population was created by transfection of B78H1 cells (no gD receptor) with expression plasmids for gB:NT, gH, gL, different versions of gD, as indicated, and split luciferase N-terminal plasmid $RLuc8_{(1-7)}$. B78-vIII (EGFRvIII-expressing) target cells were transfected with split luciferase C-terminal plasmid $RLuc8_{(8-11)}$. Upon mixing of the effector and target cell populations, luminescence resulting from glycoprotein-mediated fusion of target and effector cells was measured over time.

We used mammalian constructs to express full-length parental and mutant retargeted gDs on the surface of HSV entry-receptor-deficient mouse melanoma B78H1 cells along with glycoproteins gB:NT and gH/gL. After incubating these cells with stably EGFRvIII-transduced B78H1 cells (B78-vIII), we measured cell-cell fusion activity by split-luciferase assay at 1-h intervals over a period of 6 h. While all retargeted constructs provoked fusion between the transfected and EGFRvIII-expressing cells, the P54Q and T213M mutants showed 50% reduced activity compared to parental gD:scEΔ38 (FIG. 6A). The P54Q/T213M double mutant was further impaired for fusion (~15% activity), indicating that the mutations either compromised presentation of the retargeted gD on the cell surface or interferred directly with the ability of the modified gDs to initiate the fusion cascade.

mar Mutations Block the Ability of Site-Specific mAbs to Inhibit Cell Fusion.

Figure 6B:
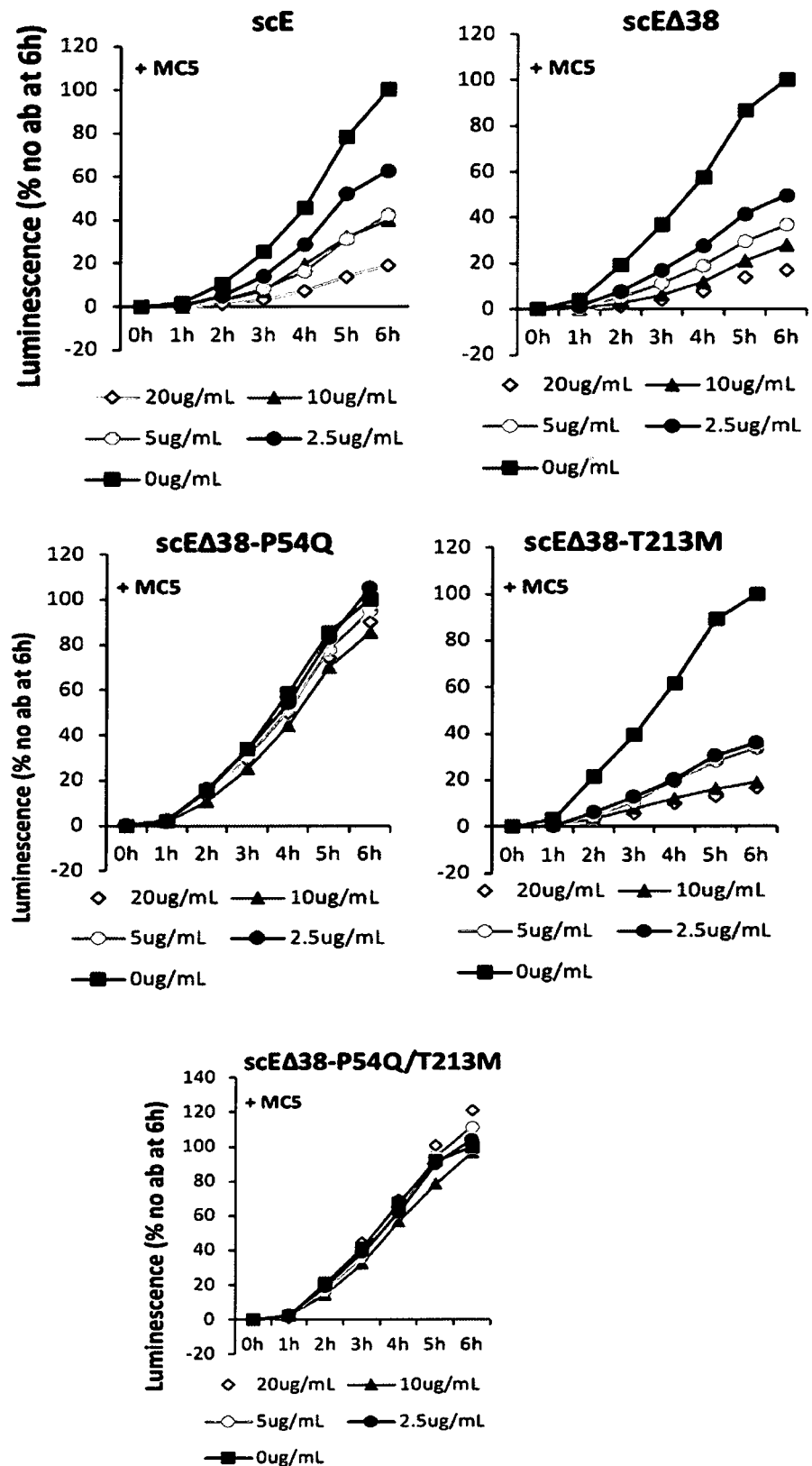
Figure 6C:
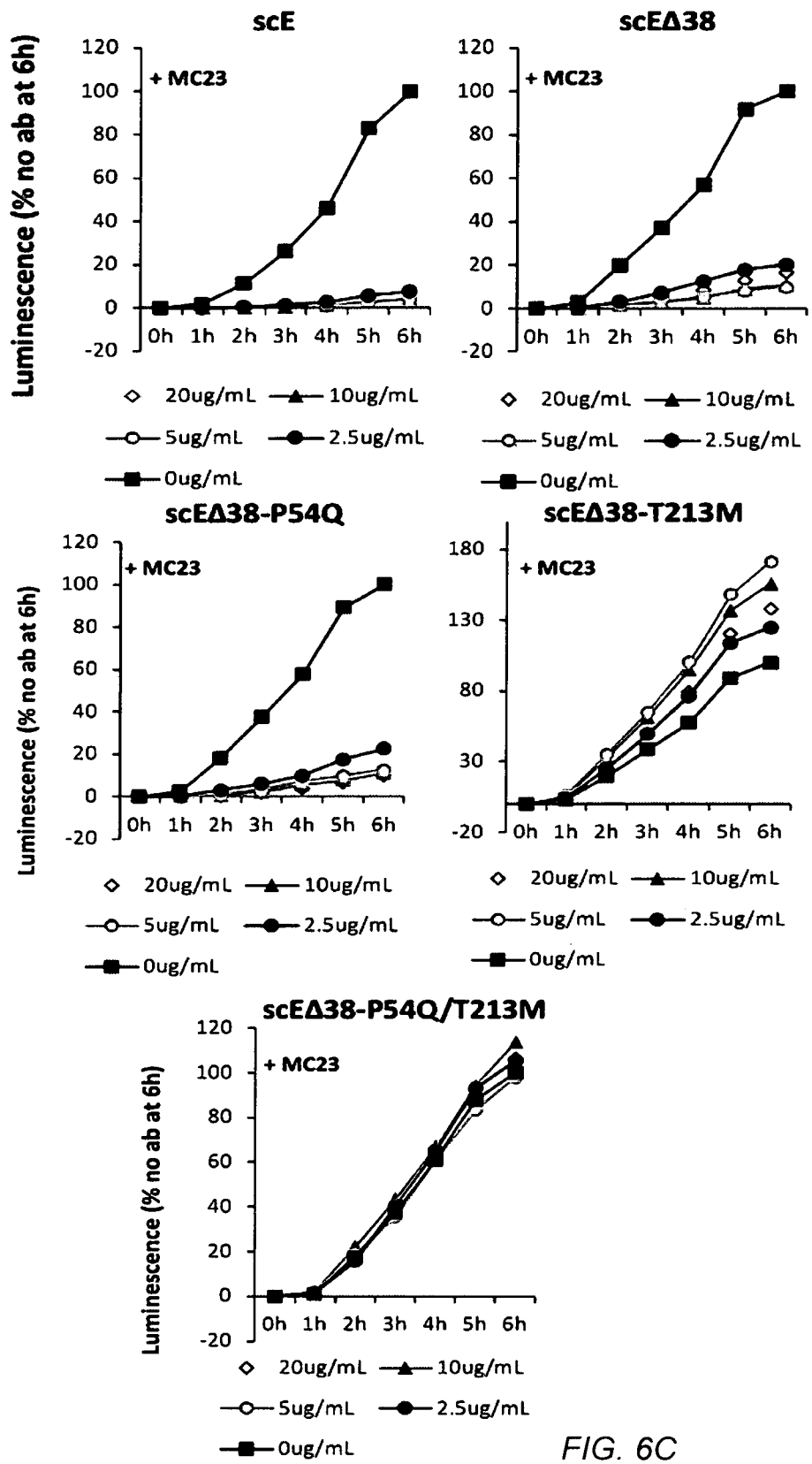

To determine whether fusion initiated by retargeted gD was sensitive to mAbs MC5 and MC23, we incubated B78H1 cells transfected with the 4 glycoprotein constructs with increasing concentrations of either mAb for 1 h before the addition of B78-vIII cells. We observed that the fusion activity of cells transfected with the parental retargeted gD construct was inhibited in a dose-dependent manner by both MC5 and MC23 (FIGS. 6B and 6C). However, the P54Q and T213M mutations reduced or completely blocked the inhibitory effects of MC5 and MC23, respectively, and the combined mutations eliminated fusion sensitivity to both mAbs (FIGS. 6B and 6C).

Virus Construction, Growth, and Entry Specificities

MC23 and MC5 are neutralizing antibodies for wt HSV-1 that appear to act at different stages of the fusion pathway, by blocking either receptor (nectin-1) binding or receptor-bound gD signaling to gH/gL, respectively. To determine whether the two mar mutations diminished retargeted virus infection, as suggested by their negative effects on cell fusion efficiency, while protecting the virus from antibodies such as MC23 and MC5, we created recombinant viruses expressing parental retargeted gD or its single or double-mutant derivatives, as described above (FIG. 3). Viruses were grown on Vero cells that naturally express both nectin-1 and simian EGFR recognized by our anti-EGFR scFv. Biological titers in PFU/µl were determined by standard plaque assays on Vero cells and physical titers in genome copies (gc)/µl were established by real-time quantitative PCR (qPCR) for the HSV-1 early gene UL5 encoding a DNA helicase-primase subunit. Comparison of gc/pfu ratios between the virus stocks suggested more efficient production of infectious virus by the unmodified retargeted virus than by its mar mutant counterparts (Table 2).

TABLE 2

| gD mar mutant | gc number/µl | PFU/µl | gc/PFU ratios |
|---|---|---|---|
| wt | 2.30E+07 | 4.20E+06 | 5.47 |
| scEΔ38 | 1.23E+07 | 1.88E+06 | 6.54 |
| scEΔ38-P54Q | 9.49E+06 | 3.04E+04 | 3.12E+2 |
| scEΔ38-T213M | 3.73E+07 | 7E+05 | 5.3E+1 |
| scEΔ38-P54Q/T213M | 5.65E+06 | 1.52E+04 | 3.71E+2 |

We also tested the entry specificities of the 4 viruses by infection of cells expressing either no gD receptor (B78H1), human nectin-1 (B78/C), or EGFRvIII (B78-vIII), using Vero cells as controls. Images of mCherry expression from the common genome backbone of these viruses at 24 h post-infection showed that none of the viruses were able to enter into B78H1 or B78/C cells, while all could enter into B78-vIII and Vero cells, confirming that entry remained strictly dependent on cellular expression of primate EGFR (FIG. 7A).

P54Q and P54Q/T213M mutants appeared to have lower entry efficiencies at MOI=1 compared to the parental retargeted and the T213M mutant (FIG. 7A), which may be related to the differences in particle (gc)/PFU ratios between the stocks of the different viruses used in this particular experiment (Table 2).

Comparison of gD Incorporation into Virus Particles Among Retargeted Virus Mutants.

We assessed gD incorporation into purified virions by Western blot analysis of equal gc, using DL6 as the primary antibody. To control for overall differences in particle contents, we also probed the blots with antibodies to gB and the tegument protein VP16. As exemplified by the results presented in FIG. 7B, retargeting reduced gD incorporation and the mar mutations, particularly when combined, enhanced this effect. gB levels did not dramatically differ between the different viruses, including non-targeted virus (gD wt), indicating that gD and gB incorporation were mutually independent. These results demonstrated that both retargeting and the mar mutations can limit the abundance of gD in mature virions, most likely a result of impaired intracellular processing of the modified proteins, reduced stability, or both.

mar Mutations Increase Resistance to Virus Neutralization by mAbs

Figure 8:
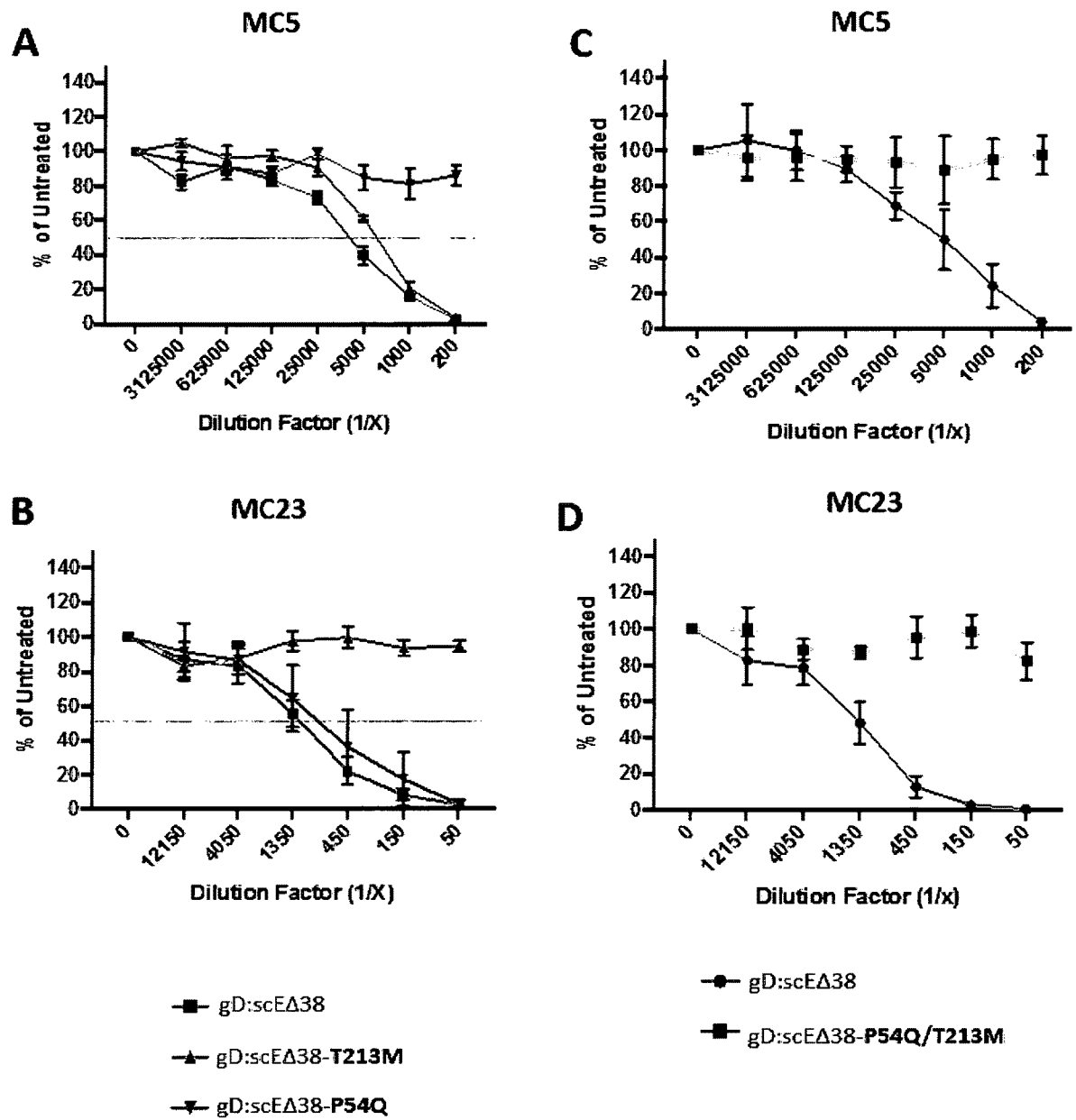
FIG. 8. Neutralization of retargeted viruses by mAbs MC5 and MC23. Viruses named below each vertical pair of panels (A, B or C, D) were incubated with virus neutralizing mAbs MC5 (A, C) or MC23 (B, D) at a range of dilutions prior to infection of Vero cells. Infected cell monolayers were overlayed with high-density medium and plaques were counted 48 h later. Representative results showing % plaque-forming units (PFU) relative to virus-only control wells (100%). (A, B) Retargeted and single-mutant retargeted viruses; (C, D) retargeted and double-mutant retargeted viruses. Data represent the means of 3 wells/condition±SEM.

We confirmed that the retargeted virus was sensitive to inactivation by mAbs MC5 and MC23 and performed additional neutralization assays to determine whether the mar mutations offered protection against these mAbs. Viruses were incubated for 90 min with serial dilutions of MC5 or MC23 prior to infection of Vero cells, and plaques were counted at 48 h. Panels A and B of FIG. 8 show that each mar mutation increased the resistance of the retargeted virus in a manner consistent with the earlier binding and fusion-inhibition results. Specifically, the P54Q mutant showed resistance to mAb MC5, and similarly, the T213M mutant was resistant to MC23. Furthermore, the P54Q/T213M double mutant was resistant to both mAbs (FIG. 8 (C, D)).

Figure 9:
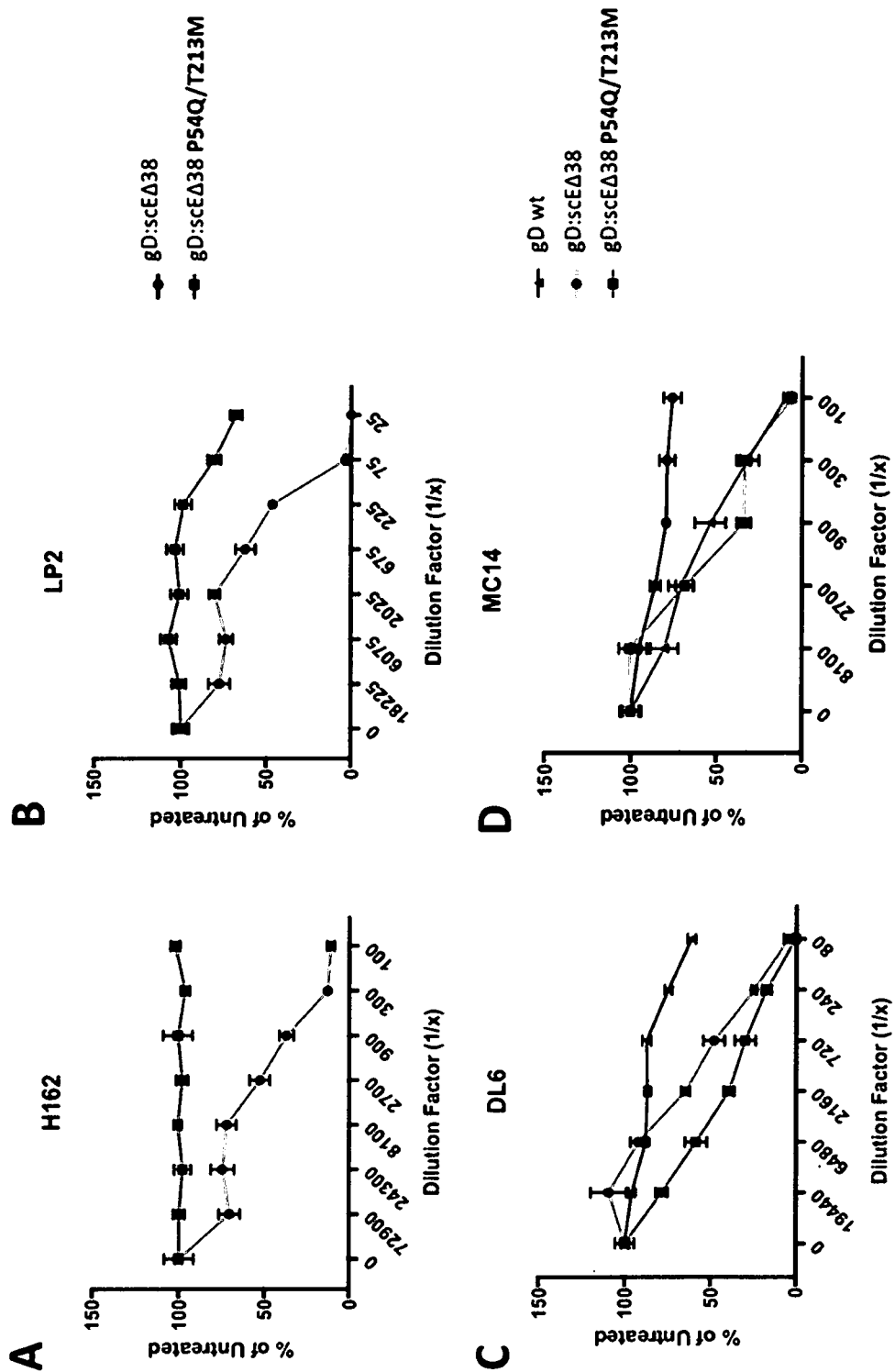
FIG. 9—Neutralization of the retargeted and double-mar mutant retargeted viruses. Both viruses were incubated with different mAbs at a range of dilutions prior to infection of Vero cells. Infected cell monolayers were overlayed with high-density medium and plaques were counted 48 h later. Representative results showing % PFU relative to virus-only control wells (100%). Neutralization of the retargeted virus (gD:scEΔ38) and double-mar mutant retargeted virus (gD:scEΔ38 P54Q/T213M) with A, mAb H162; B, mAb LP2; C, mAb DL6; and D, mAb MC14. KNTc expressing wt gD is included in panels C and D for comparison (gD wt). Data is shown as the mean of triplicate wells±SEM.

We expanded these results by examining the resistance of the double-mutant retargeted virus to VN by two other mAbs, H162 from the same group as MC5 (blue), and LP2 from the same group as MC23 (red). H162, whose binding to retargeted gD was abolished by the double mutation (FIG. 5(D)), neutralized the retargeted virus while the double mutant was fully protected (FIG. 9(A)). Similarly, the mutations caused increased resistance to LP2 although some remaining sensitivity at the lower mAb dilutions was evident (FIG. 9(B)), consistent with low residual binding of LP2 to the double-mutant retargeted gD (FIG. 5(D)). Thus, the effects of the mutations on virus neutralization were not limited to single representatives of the blue and red mAb groups.

Figure 5:
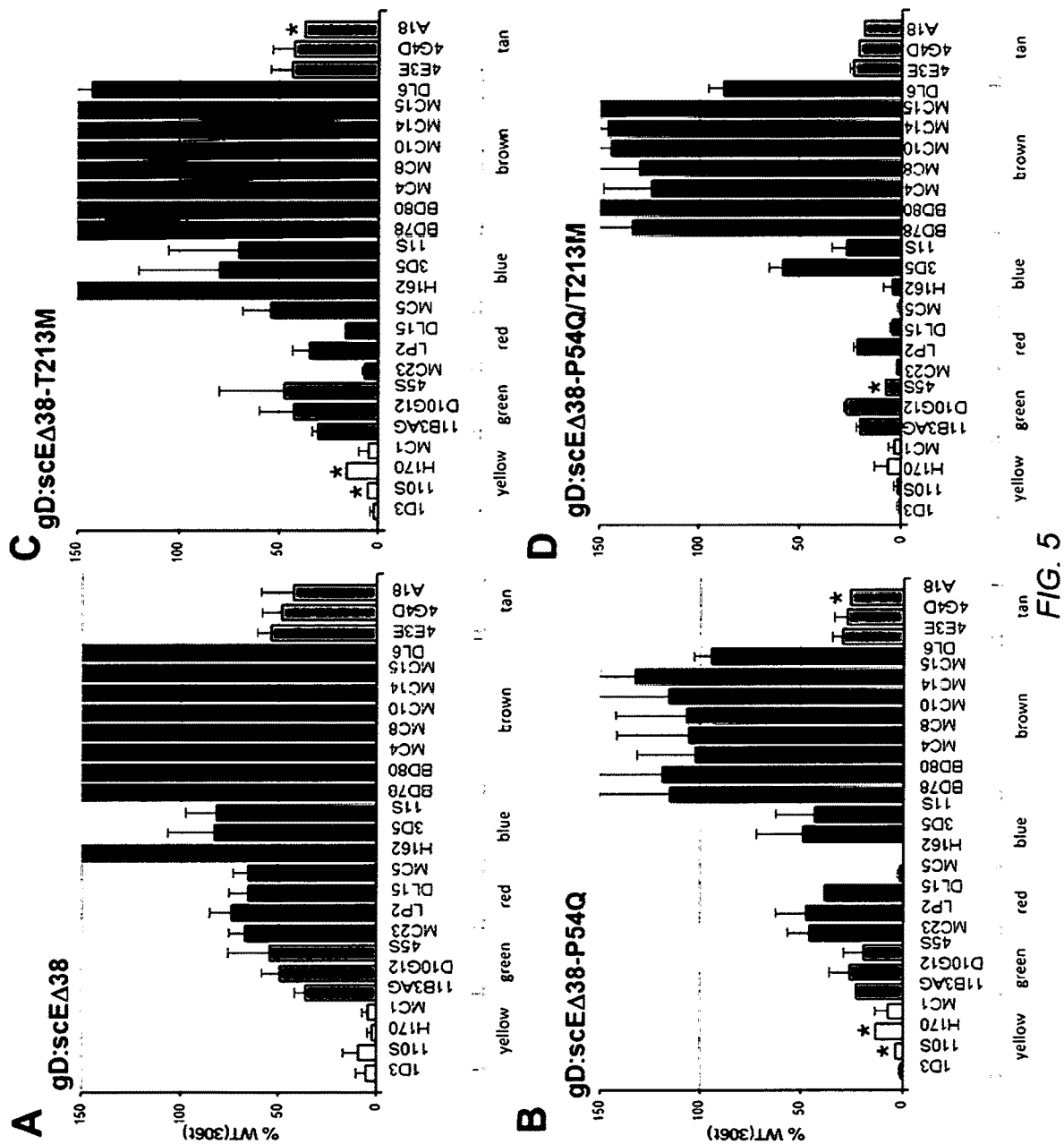
FIG. 5. Effects of retargeting and monoclonal antibody (mAb) resistance (mar) mutations on mAb binding to purified gD ectodomains (ECDs). Sequences encoding the ECDs of gD:scEΔ38 and its mar mutants were cloned into a baculovirus expression plasmid, pVTBac. Sf9 insect cells were transfected with these plasmids along with linearized baculovirus DNA to produce recombinant baculoviruses. Individual isolates were tested by WB for gD ECD production and the highest producer clones were used for larger scale protein production. Soluble proteins were purified through an anti-gD (DL6) column. Binding of 25 gD-specific mAbs to each purified ECD was analyzed by surface plasmon resonance imaging (SPRi) and data for binding of retargeted (A) or mutant retargeted gD (B-D) by each anti-gD mAb are shown as a percentage relative to wt gD (100%). Each mAb is named below the horizontal axis; mAbs to the same or overlapping epitopes are grouped and each group is referred to by a distinct color (Cairns 2017), as indicated below the mAb names. Values are the means±SEM of 2-5 independent determinations, except those denoted by (*) that were determined just once. A. gD:scEΔ38; B. gD:scEΔ38-P54Q; C. gD:scEΔ38-T213M; D. gD:scEΔ38-P54Q/T213M.

Since the SPRi results revealed increased binding of all or nearly all of the mAbs of the brown group to retargeted and double-mutant retargeted gD compared to wt gD (FIG. 5 (A, D)), we tested 2 of the brown mAbs for neutralization of viruses containing these different versions of gD. The results (FIG. 9 (C, D)) showed that both mAbs were neutralizing for both of the retargeted viruses, while the non-retargeted virus expressing wt gD was substantially less sensitive to either mAb. We suggest that these mAbs gain neutralizing activity through increased accessibility of their epitope(s) caused by the retargeting modifications and that the P54Q/T213M double mutation does not restore the protected wt conformation of this region to reduce or reverse this effect.

It should be noted that human immune sera typically do not block the binding of mAbs from the brown group (e.g., MC14) to wt gD (Cairns et al, 2015), suggesting that HSV-immune individuals do not contain antibodies to the brown epitope(s) of retargeted gD.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A retargeted herpes simplex virus (HSV) particle, comprising a genome, a capsid, tegument, and an envelope comprising an antigenically-modified glycoprotein D (gD) protein, wherein one or more of amino acids 10-20, 54, 75-79, 132, 140, 213, 216, 222-224, and 262-279 of SEQ ID NO: 1 or SEQ ID NO: 2, or one or more amino acids corresponding to amino acids 10-20, 54, 75-79, 132, 140, 213, 216, 222-224, and 262-279 of SEQ ID NO: 1 or SEQ ID NO: 2, are modified in the gD glycoprotein of the virus particle, and wherein the modifications:

reduce or eliminate neutralization of the retargeted virus particle by antibodies that recognize the gD glycoprotein, and permit gD glycoprotein-mediated infection of a target cell by the retargeted virus particle.

2. The virus particle of claim 1, wherein one or both of amino acids P54 and T213 of SEQ ID NO: 1 or SEQ ID NO: 2, or one or both amino acids corresponding to amino acids P54 and T213 of SEQ ID NO: 1 or SEQ ID NO: 2 are modified.

3. The virus particle of claim 1, further comprising an antigenically-modified glycoprotein B (gB), wherein the modification is in one of more of amino acids 47, 62, 85, 203, 303, 304, 305, 308, 328, 335, 419, 473, 594, or 640-670 of SEQ ID NO: 3 or amino acid 412 of SEQ ID NO: 4, or one or more amino acids corresponding to amino acids 47, 62, 85, 203, 303, 304, 305, 308, 328, 335, 419, 473, 594, or 640-670 of SEQ ID NO: 3 or amino acid 412 of SEQ ID NO: 4.

4. The virus particle of claim 1, having a 438 mutation of SEQ ID NO: 1 or 2, or a mutation in a gD glycoprotein corresponding to a 438 mutation of SEQ ID NO: 1 or 2.

5. The virus particle of claim 1, comprising a non-native ligand capable of binding a surface component of a target cell type.

6. The virus particle of claim 5, wherein the target cell type is a cancer cell.

7. The virus particle of claim 5, wherein the non-native ligand capable of binding a surface component of a target cell type is incorporated into a viral envelope glycoprotein of the virus particle.

8. The virus particle of claim 7, wherein the viral envelope glycoprotein of the virus particle into which the ligand is incorporated is gD, gC, gB and/or gH.

9. The virus particle of claim 5, wherein the surface component is one or more of EGFR, EGFRvIII, other oncogenic EGFR variants, HER2, CD133, CXCR4, carcinoembryonic antigen (CEA), CLC-3/annexin-2/MMP-2, human transferrin receptor, EpCAM, or c-Met.

10. The virus particle of claim 1, wherein binding of at least one or more viral envelope glycoproteins to its natural receptor is eliminated.

11. The virus particle of claim 1, wherein the genome comprises an exogenous expression cassette.

12. The virus particle of claim 11, wherein the exogenous expression cassette encodes an agent that enhances tumor killing activity.

13. The virus particle of claim 1, wherein the genome comprises a target sequence for one or more microRNAs.

14. A recombinant HSV genome encoding the virus particle of claim 1.

15. A viral stock, comprising at least $10^5$ pfus of a virus particle of claim 1.

16. A pharmaceutical dosage form comprising at least $10^5$ pfus of a virus particle of claim 1, and a pharmaceutically-acceptable excipient.

17. The dosage form of claim 16, formulated for parenteral delivery.

18. A method of treating a patient having a cancer, comprising administering to the patient an amount of the virus particle of claim 6 effective to treat a cancer patient.

19. The virus particle of claim 2, wherein the modifications to SEQ ID NO: 1 or SEQ ID NO: 2 comprise P54Q and/or T213M.

20. A retargeted herpes simplex virus (HSV) particle, comprising a genome, a capsid, tegument, and an envelope comprising an antigenically-modified glycoprotein D (gD) protein, wherein the antigenically-modified gD protein comprises a P54Q and/or a T213M substitution in SEQ ID NO: 1 or SEQ ID NO: 2 and optionally one or more of amino acids 10-20, 75-79, 132, 140, 216, 222-224, and 262-279 of SEQ ID NO: 1 or SEQ ID NO: 2, or one or more amino acids corresponding to amino acids 10-20, 75-79, 132, 140, 216, 222-224, and 262-279 of SEQ ID NO: 1 or SEQ ID NO: 2, are modified in the gD glycoprotein of the virus particle, and wherein the modifications:
  reduce or eliminate neutralization of the retargeted virus particle by antibodies that recognize the gD glycoprotein, and
  permit infection of a target cell by the retargeted virus particle.

21. The virus particle of claim 20, further comprising an antigenically-modified glycoprotein B (gB), wherein the modification is in one of more of amino acids 47, 62, 85, 203, 303, 304, 305, 308, 328, 335, 419, 473, 594, or 640-670 of SEQ ID NO: 3, or amino acid 412 of SEQ ID NO: 4, or one or more amino acids corresponding to amino acids 47, 62, 85, 203, 303, 304, 305, 308, 328, 335, 419, 473, 594, or 640-670 of SEQ ID NO: 3, or amino acid 412 of SEQ ID NO: 4.

* * * * *

UNITED STATES PATENT AND TRADEMARK OFFICE
CERTIFICATE OF CORRECTION

PATENT NO. : 12,414,973 B2  
APPLICATION NO. : 17/058379  
DATED : September 16, 2025  
INVENTOR(S) : Joseph C. Glorioso, III et al.

Page 1 of 1

It is certified that error appears in the above-identified patent and that said Letters Patent is hereby corrected as shown below:

In the Claims

Column 45, Line 56, Claim 4, delete "438" and insert -- Δ38 --

Column 45, Line 58, Claim 4, delete "438" and insert -- Δ38 --

Signed and Sealed this  
Eleventh Day of November, 2025

John A. Squires  
*Director of the United States Patent and Trademark Office*

SEQUENCE LISTING

<160> NUMBER OF SEQ ID NOS: 15

<210> SEQ ID NO 1
<211> LENGTH: 369
<212> TYPE: PRT
<213> ORGANISM: herpes simplex virus

<400> SEQUENCE: 1

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

```
Pro His Ile Arg Glu Asp Asp Gln Pro Ser Ser His Gln Pro Leu Phe
        355                 360                 365

Tyr

<210> SEQ ID NO 2
<211> LENGTH: 368
<212> TYPE: PRT
<213> ORGANISM: herpes simplex virus

<400> SEQUENCE: 2

Lys Tyr Ala Leu Ala Asp Pro Ser Leu Lys Met Ala Asp Pro Asn Arg
1               5                   10                  15

Phe Arg Gly Lys Asn Leu Pro Val Leu Asp Gln Leu Thr Asp Pro Pro
            20                  25                  30

Gly Val Lys Arg Val Tyr His Ile Gln Pro Ser Leu Glu Asp Pro Phe
        35                  40                  45

Gln Pro Pro Ser Ile Pro Ile Thr Val Tyr Tyr Ala Val Leu Glu Arg
    50                  55                  60

Ala Cys Arg Ser Val Leu Leu His Ala Pro Ser Glu Ala Pro Gln Ile
65                  70                  75                  80

Val Arg Gly Ala Ser Asp Glu Ala Arg Lys His Thr Tyr Asn Leu Thr
                85                  90                  95

Ile Ala Trp Tyr Arg Met Gly Asp Asn Cys Ala Ile Pro Ile Thr Val
            100                 105                 110

Met Glu Tyr Thr Glu Cys Pro Tyr Asn Lys Ser Leu Gly Val Cys Pro
        115                 120                 125

Ile Arg Thr Gln Pro Arg Trp Ser Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
        275                 280                 285

Gln Ile Pro Pro Asn Trp His Ile Pro Ser Ile Gln Asp Val Ala Pro
    290                 295                 300

His His Ala Pro Ala Ala Pro Ser Asn Pro Gly Leu Ile Ile Gly Ala
305                 310                 315                 320

Leu Ala Gly Ser Thr Leu Ala Val Leu Val Ile Gly Gly Ile Ala Phe
                325                 330                 335

Trp Val Arg Arg Arg Ala Gln Met Ala Pro Lys Arg Leu Arg Leu Pro
            340                 345                 350
```

His Ile Arg Asp Asp Ala Pro Pro Ser His Gln Pro Leu Phe Tyr
                355                 360                 365

<210> SEQ ID NO 3
<211> LENGTH: 904
<212> TYPE: PRT
<213> ORGANISM: herpes simplex virus

<400> SEQUENCE: 3

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Thr Ser Pro Gly Thr Pro Gly Val Ala Ala Thr Gln Ala Ala Asn
        35                  40                  45

Gly Gly Pro Ala Thr Pro Ala Pro Pro Leu Gly Ala Ala Pro Thr
    50                  55                  60

Gly Asp Pro Lys Pro Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

```
Ala Trp Asp Trp Val Pro Lys Arg Pro Ser Val Cys Thr Met Thr Lys
        355                 360                 365
Trp Gln Glu Val Asp Glu Met Leu Arg Ser Glu Tyr Gly Gly Ser Phe
    370                 375                 380
Arg Phe Ser Ser Asp Ala Ile Ser Thr Thr Phe Thr Thr Asn Leu Thr
385                 390                 395                 400
Glu Tyr Pro Leu Ser Arg Val Asp Leu Gly Asp Cys Ile Gly Lys Asp
                405                 410                 415
Ala Arg Asp Ala Met Asp Arg Ile Phe Ala Arg Arg Tyr Asn Ala Thr
                420                 425                 430
His Ile Lys Val Gly Gln Pro Gln Tyr Tyr Gln Ala Asn Gly Gly Phe
            435                 440                 445
Leu Ile Ala Tyr Gln Pro Leu Leu Ser Asn Thr Leu Ala Glu Leu Tyr
        450                 455                 460
Val Arg Glu His Leu Arg Glu Gln Ser Arg Lys Pro Pro Asn Pro Thr
465                 470                 475                 480
Pro Pro Pro Pro Gly Ala Ser Ala Asn Ala Ser Val Glu Arg Ile Lys
                485                 490                 495
Thr Thr Ser Ser Ile Glu Phe Ala Arg Leu Gln Phe Thr Tyr Asn His
            500                 505                 510
Ile Gln Arg His Val Asn Asp Met Leu Gly Arg Val Ala Ile Ala Trp
        515                 520                 525
Cys Glu Leu Gln Asn His Glu Leu Thr Leu Trp Asn Glu Ala Arg Lys
    530                 535                 540
Leu Asn Pro Asn Ala Ile Ala Ser Val Thr Val Gly Arg Arg Val Ser
545                 550                 555                 560
Ala Arg Met Leu Gly Asp Val Met Ala Val Ser Thr Cys Val Pro Val
                565                 570                 575
Ala Ala Asp Asn Val Ile Val Gln Asn Ser Met Arg Ile Ser Ser Arg
                580                 585                 590
Pro Gly Ala Cys Tyr Ser Arg Pro Leu Val Ser Phe Arg Tyr Glu Asp
            595                 600                 605
Gln Gly Pro Leu Val Glu Gly Gln Leu Gly Glu Asn Asn Glu Leu Arg
        610                 615                 620
Leu Thr Arg Asp Ala Ile Glu Pro Cys Thr Val Gly His Arg Arg Tyr
625                 630                 635                 640
Phe Thr Phe Gly Gly Gly Tyr Val Tyr Phe Glu Glu Tyr Ala Tyr Ser
                645                 650                 655
His Gln Leu Ser Arg Ala Asp Ile Thr Thr Val Ser Thr Phe Ile Asp
            660                 665                 670
Leu Asn Ile Thr Met Leu Glu Asp His Glu Phe Val Pro Leu Glu Val
        675                 680                 685
Tyr Thr Arg His Glu Ile Lys Asp Ser Gly Leu Leu Asp Tyr Thr Glu
    690                 695                 700
Val Gln Arg Arg Asn Gln Leu His Asp Leu Arg Phe Ala Asp Ile Asp
705                 710                 715                 720
Thr Val Ile His Ala Asp Ala Asn Ala Ala Met Phe Ala Gly Leu Gly
                725                 730                 735
Ala Phe Phe Glu Gly Met Gly Asp Leu Gly Arg Ala Val Gly Lys Val
                740                 745                 750
Val Met Gly Ile Val Gly Gly Val Val Ser Ala Val Ser Gly Val Ser
            755                 760                 765
```

-continued

```
Ser Phe Met Ser Asn Pro Phe Gly Ala Leu Ala Val Gly Leu Leu Val
770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Gly
                820                 825                 830

Gly Asp Phe Asp Glu Ala Lys Leu Ala Glu Ala Arg Glu Met Ile Arg
                835                 840                 845

Tyr Met Ala Leu Val Ser Ala Met Glu Arg Thr Glu His Lys Ala Lys
850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
                900

<210> SEQ ID NO 4
<211> LENGTH: 902
<212> TYPE: PRT
<213> ORGANISM: herpes simplex virus

<400> SEQUENCE: 4

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
                20                  25                  30

Ser Gly Ala Trp Pro Thr Val Ala Asn Gly Gly Pro Ala Ser Arg Pro
                35                  40                  45

Pro Pro Val Pro Ser Pro Ala Thr Thr Lys Ala Arg Lys Arg Lys Thr
                50                  55                  60

Lys Lys Pro Pro Lys Arg Pro Glu Ala Thr Pro Pro Asp Ala Asn
65              70                  75                  80

Ala Thr Val Ala Ala Gly His Ala Thr Leu Arg Ala His Leu Arg Glu
                85                  90                  95

Ile Lys Val Glu Asn Ala Asp Ala Gln Phe Tyr Val Cys Pro Pro Pro
                100                 105                 110

Thr Gly Ala Thr Val Val Gln Phe Glu Gln Pro Arg Arg Cys Pro Thr
                115                 120                 125

Arg Pro Glu Gly Gln Asn Tyr Thr Glu Gly Ile Ala Val Val Phe Lys
                130                 135                 140

Glu Asn Ile Ala Pro Tyr Lys Phe Lys Ala Thr Met Tyr Tyr Lys Asp
145                 150                 155                 160

Val Thr Val Ser Gln Val Trp Phe Gly His Arg Tyr Ser Gln Phe Met
                165                 170                 175

Gly Ile Phe Glu Asp Arg Ala Pro Val Pro Phe Glu Glu Val Ile Asp
                180                 185                 190

Lys Ile Asn Ala Lys Gly Val Cys Arg Ser Thr Ala Lys Tyr Val Arg
                195                 200                 205

Asn Asn Met Glu Thr Thr Ala Phe His Arg Asp Asp His Glu Thr Asp
                210                 215                 220

Met Glu Leu Lys Pro Ala Lys Val Ala Thr Arg Thr Ser Arg Gly Trp
225                 230                 235                 240
```

```
His Thr Thr Asp Leu Lys Tyr Asn Pro Ser Arg Val Glu Ala Phe His
            245                 250                 255

Arg Tyr Gly Thr Thr Val Asn Cys Ile Val Glu Val Asp Ala Arg
        260                 265                 270

Ser Val Tyr Pro Tyr Asp Glu Phe Val Leu Ala Thr Gly Asp Phe Val
            275                 280                 285

Tyr Met Ser Pro Phe Tyr Gly Tyr Arg Glu Gly Ser His Thr Glu His
        290                 295                 300

Thr Thr Tyr Ala Ala Asp Arg Phe Lys Gln Val Asp Gly Phe Tyr Ala
305                 310                 315                 320

Arg Asp Leu Thr Thr Lys Ala Arg Ala Thr Ser Pro Thr Arg Asn
                325                 330                 335

Leu Leu Thr Thr Pro Lys Phe Thr Val Ala Trp Asp Trp Val Pro Lys
            340                 345                 350

Arg Pro Ala Val Cys Thr Met Thr Lys Trp Gln Glu Val Asp Glu Met
        355                 360                 365

Leu Arg Ala Glu Tyr Gly Gly Ser Phe Arg Phe Ser Ser Asp Ala Ile
        370                 375                 380

Ser Thr Thr Phe Thr Thr Asn Leu Thr Gln Tyr Ser Leu Ser Arg Val
385                 390                 395                 400

Asp Leu Gly Asp Cys Ile Gly Arg Asp Ala Arg Glu Ala Ile Asp Arg
                405                 410                 415

Met Phe Ala Arg Lys Tyr Asn Ala Thr His Ile Lys Val Gly Gln Pro
            420                 425                 430

Gln Tyr Tyr Leu Ala Thr Gly Gly Phe Leu Ile Ala Tyr Gln Pro Leu
        435                 440                 445

Leu Ser Asn Thr Leu Ala Glu Leu Tyr Val Arg Glu Tyr Met Arg Glu
        450                 455                 460

Gln Asp Arg Lys Pro Arg Asn Ala Thr Ala Pro Leu Arg Glu Arg
465                 470                 475                 480

Pro Ser Ala Asn Ala Ser Val Glu Arg Ile Lys Thr Thr Ser Ser Ile
                485                 490                 495

Glu Phe Ala Arg Leu Gln Phe Thr Tyr Asn His Ile Arg His Val
            500                 505                 510

Asn Asp Met Leu Gly Arg Ile Ala Val Ala Trp Cys Glu Leu Gln Asn
        515                 520                 525

His Glu Leu Thr Leu Trp Asn Glu Ala Arg Lys Leu Asn Pro Asn Ala
        530                 535                 540

Ile Ala Ser Ala Thr Val Gly Arg Arg Val Ser Ala Arg Met Leu Gly
545                 550                 555                 560

Asp Val Met Ala Val Ser Thr Cys Val Pro Val Ala Pro Asp Asn Val
                565                 570                 575

Ile Val Gln Asn Ser Met Arg Val Ser Ser Arg Pro Gly Thr Cys Tyr
            580                 585                 590

Ser Arg Pro Leu Val Ser Phe Arg Tyr Glu Asp Gln Gly Pro Leu Met
        595                 600                 605

Glu Gly Gln Leu Gly Glu Asn Asn Glu Leu Arg Leu Thr Arg Asp Ala
        610                 615                 620

Leu Glu Pro Cys Thr Val Gly His Arg Arg Tyr Phe Ile Phe Gly Gly
625                 630                 635                 640

Gly Tyr Val Tyr Phe Glu Glu Tyr Ala Tyr Ser His Gln Leu Ser Arg
                645                 650                 655
```

```
Ala Asp Val Thr Thr Val Arg Thr Phe Ile Asp Leu Asn Ile Thr Met
            660                 665                 670

Leu Glu Asp His Glu Phe Val Pro Leu Glu Val Tyr Thr Arg His Glu
            675                 680                 685

Ile Lys Asp Ser Gly Leu Leu Asp Tyr Thr Glu Val Gln Arg Arg Asn
            690                 695                 700

Gln Leu His Asp Leu Arg Phe Ala Asp Ile Asp Thr Val Ile Arg Ala
705                 710                 715                 720

Asp Ala Asn Ala Ala Met Phe Ala Gly Leu Cys Ala Phe Phe Glu Gly
                725                 730                 735

Met Gly Asp Leu Gly Arg Ala Val Gly Lys Val Val Met Gly Val Val
            740                 745                 750

Gly Gly Val Val Ser Ala Val Ser Gly Val Ser Ser Phe Met Ser Asn
            755                 760                 765

Pro Phe Gly Ala Leu Ala Val Gly Leu Leu Val Leu Ala Gly Leu Val
            770                 775                 780

Ala Ala Phe Phe Ala Phe Arg Tyr Val Leu Gln Leu Gln Arg Asn Pro
785                 790                 795                 800

Met Lys Ala Leu Tyr Pro Leu Thr Thr Lys Glu Leu Lys Thr Ser Asp
                805                 810                 815

Pro Gly Gly Val Gly Gly Glu Gly Glu Glu Gly Ala Glu Gly Gly Gly
            820                 825                 830

Phe Asp Glu Ala Lys Leu Ala Glu Ala Arg Glu Met Ile Arg Tyr Met
            835                 840                 845

Ala Leu Val Ser Ala Met Glu Arg Thr Glu His Lys Ala Arg Lys Lys
850                 855                 860

Gly Thr Ser Ala Leu Leu Ser Ser Lys Val Thr Asn Met Val Leu Arg
865                 870                 875                 880

Lys Arg Asn Lys Ala Arg Tyr Ser Pro Leu His Asn Glu Asp Glu Ala
                885                 890                 895

Gly Asp Glu Asp Glu Leu
            900

<210> SEQ ID NO 5
<211> LENGTH: 625
<212> TYPE: PRT
<213> ORGANISM: herpes simplex virus

<400> SEQUENCE: 5

Met Gly Gly Ala Ala Ala Arg Leu Gly Ala Val Ile Leu Phe Val Val
1               5                   10                  15

Ile Val Gly Leu His Gly Val Arg Ser Lys Asp Ile Leu Met Thr Gln
            20                  25                  30

Ser Pro Leu Ser Leu Pro Val Ser Leu Gly Asp Gln Ala Ser Ile Ser
        35                  40                  45

Cys Arg Ser Ser Gln Asn Ile Val His Asn Asn Gly Ile Thr Tyr Leu
    50                  55                  60

Glu Trp Tyr Leu Gln Arg Pro Gly Gln Ser Pro Lys Leu Leu Ile Tyr
65                  70                  75                  80

Lys Val Ser Asp Arg Phe Ser Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Leu Gly Ile Tyr Tyr Cys Phe Gln Gly Ser His Ile Pro Pro Thr
            115                 120                 125
```

```
Phe Gly Gly Gly Thr Lys Leu Glu Ile Lys Arg Ala Gly Gly Gly
            130                 135                 140
Gly Ser Gly Gly Gly Ser Gly Gly Gly Ser Gln Val Gln Leu
145                 150                 155                 160
Gln Gln Ser Gly Ser Glu Met Ala Arg Pro Gly Ala Ser Val Lys Leu
                    165                 170                 175
Pro Cys Lys Ala Ser Gly Asp Thr Phe Thr Ser Tyr Trp Met His Trp
                180                 185                 190
Val Lys Gln Arg His Gly His Gly Pro Glu Trp Ile Gly Asn Ile Tyr
            195                 200                 205
Pro Gly Ser Gly Gly Thr Asn Tyr Ala Glu Lys Phe Lys Asn Lys Val
        210                 215                 220
Thr Leu Thr Val Asp Arg Ser Ser Arg Thr Val Tyr Met His Leu Ser
225                 230                 235                 240
Arg Leu Thr Ser Glu Asp Ser Ala Val Tyr Tyr Cys Thr Arg Ser Gly
                245                 250                 255
Gly Pro Tyr Phe Phe Asp Tyr Trp Gly Gln Gly Thr Thr Leu Thr Val
                260                 265                 270
Ser Ser Gly Gly Gly Gly Ser Gly Ser Leu Asp Gln Leu Thr Asp Pro
            275                 280                 285
Pro Gly Val Arg Arg Val His Ile Gln Ala Gly Leu Pro Asp Pro Phe
        290                 295                 300
Gln Pro Pro Ser Leu Pro Ile Thr Val Tyr Tyr Ala Val Leu Glu Arg
305                 310                 315                 320
Ala Cys Arg Ser Val Leu Leu Asn Ala Pro Ser Glu Ala Pro Gln Ile
                325                 330                 335
Val Arg Gly Ala Ser Glu Asp Val Arg Lys Gln Pro Tyr Asn Leu Thr
            340                 345                 350
Ile Ala Trp Phe Arg Met Gly Gly Asn Cys Ala Ile Pro Ile Thr Val
        355                 360                 365
Met Glu Tyr Thr Glu Cys Ser Tyr Asn Lys Ser Leu Gly Ala Cys Pro
370                 375                 380
Ile Arg Thr Gln Pro Arg Trp Asn Tyr Tyr Asp Ser Phe Ser Ala Val
385                 390                 395                 400
Ser Glu Asp Asn Leu Gly Phe Leu Met His Ala Pro Ala Phe Glu Thr
                405                 410                 415
Ala Gly Thr Tyr Leu Arg Leu Val Lys Ile Asn Asp Trp Thr Glu Ile
            420                 425                 430
Thr Gln Phe Ile Leu Glu His Arg Ala Lys Gly Ser Cys Lys Tyr Ala
        435                 440                 445
Leu Pro Leu Arg Ile Pro Pro Ser Ala Cys Leu Ser Pro Gln Ala Tyr
450                 455                 460
Gln Gln Gly Val Thr Val Asp Ser Ile Gly Met Leu Pro Arg Phe Ile
465                 470                 475                 480
Pro Glu Asn Gln Arg Thr Val Ala Val Tyr Ser Leu Lys Ile Ala Gly
                485                 490                 495
Trp His Gly Pro Lys Ala Pro Tyr Thr Ser Thr Leu Leu Pro Pro Glu
            500                 505                 510
Leu Ser Glu Thr Pro Asn Ala Thr Gln Pro Glu Leu Ala Pro Glu Asp
        515                 520                 525
Pro Glu Asp Ser Ala Leu Leu Glu Asp Pro Val Gly Thr Val Ala Pro
530                 535                 540
```

-continued

Gln Ile Pro Pro Asn Trp His Ile Pro Ser Ile Gln Asp Ala Ala Thr
545                 550                 555                 560

Pro Tyr His Pro Pro Ala Thr Pro Asn Asn Met Gly Leu Ile Ala Gly
                565                 570                 575

Ala Val Gly Gly Ser Leu Leu Ala Ala Leu Val Ile Cys Gly Ile Val
            580                 585                 590

Tyr Trp Met His Arg Arg Thr Arg Lys Ala Pro Lys Arg Ile Arg Leu
        595                 600                 605

Pro His Ile Arg Glu Asp Asp Gln Pro Ser Ser His Gln Pro Leu Phe
610                 615                 620

Tyr
625

<210> SEQ ID NO 6
<211> LENGTH: 248
<212> TYPE: PRT
<213> ORGANISM: herpes simplex virus

<400> SEQUENCE: 6

Asp Ile Leu Met Thr Gln Ser Pro Leu Ser Leu Pro Val Ser Leu Gly
1               5                   10                  15

Asp Gln Ala Ser Ile Ser Cys Arg Ser Ser Gln Asn Ile Val His Asn
            20                  25                  30

Asn Gly Ile Thr Tyr Leu Glu Trp Tyr Leu Gln Arg Pro Gly Gln Ser
        35                  40                  45

Pro Lys Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Ile Pro Pro Thr Phe Gly Gly Gly Thr Lys Leu Glu Ile Lys
            100                 105                 110

Arg Ala Ala Gly Gly Gly Gly Ser Gly Gly Gly Ser Gly Gly Gly
        115                 120                 125

Gly Ser Gln Val Gln Leu Gln Gln Ser Gly Ser Glu Met Ala Arg Pro
130                 135                 140

Gly Ala Ser Val Lys Leu Pro Cys Lys Ala Ser Gly Asp Thr Phe Thr
145                 150                 155                 160

Ser Tyr Trp Met His Trp Val Lys Gln Arg His Gly His Gly Pro Glu
                165                 170                 175

Trp Ile Gly Asn Ile Tyr Pro Gly Ser Gly Gly Thr Asn Tyr Ala Glu
            180                 185                 190

Lys Phe Lys Asn Lys Val Thr Leu Thr Val Asp Arg Ser Ser Arg Thr
        195                 200                 205

Val Tyr Met His Leu Ser Arg Leu Thr Ser Glu Asp Ser Ala Val Tyr
    210                 215                 220

Tyr Cys Thr Arg Ser Gly Gly Pro Tyr Phe Phe Asp Tyr Trp Gly Gln
225                 230                 235                 240

Gly Thr Thr Leu Thr Val Ser Ser
                245

<210> SEQ ID NO 7
<211> LENGTH: 36
<212> TYPE: DNA
<213> ORGANISM: Artificial Sequence

```
<220> FEATURE:
<223> OTHER INFORMATION: pVT Bac gD:scEGFR 5' primer

<400> SEQUENCE: 7
ccagcccggg caaagacatt ctaatgaccc aatctc                                36

<210> SEQ ID NO 8
<211> LENGTH: 39
<212> TYPE: DNA
<213> ORGANISM: Artificial Sequence
<220> FEATURE:
<223> OTHER INFORMATION: pVT Bac gD:scEGFR 3' Primer

<400> SEQUENCE: 8
ggtatgcggc cgcttaatgg taaggcgtcg cggcgtcct                             39

<210> SEQ ID NO 9
<211> LENGTH: 31
<212> TYPE: DNA
<213> ORGANISM: Artificial Sequence
<220> FEATURE:
<223> OTHER INFORMATION: SallEGFRvIIIF primer

<400> SEQUENCE: 9
gactagtcga caattcgttg gccgcatgcg a                                     31

<210> SEQ ID NO 10
<211> LENGTH: 38
<212> TYPE: DNA
<213> ORGANISM: Artificial Sequence
<220> FEATURE:
<223> OTHER INFORMATION: XholEGFRvIIIR primer

<400> SEQUENCE: 10
cactactcga gtcatgctcc aataaattca ctgctttg                              38

<210> SEQ ID NO 11
<211> LENGTH: 21
<212> TYPE: DNA
<213> ORGANISM: Artificial Sequence
<220> FEATURE:
<223> OTHER INFORMATION: UL5F primer

<400> SEQUENCE: 11
acgagcgtgg tgcggtcatg g                                                21

<210> SEQ ID NO 12
<211> LENGTH: 24
<212> TYPE: DNA
<213> ORGANISM: Artificial Sequence
<220> FEATURE:
<223> OTHER INFORMATION: UL5R primer

<400> SEQUENCE: 12
gcgggttaat agacaatgac cacg                                             24

<210> SEQ ID NO 13
<211> LENGTH: 20
<212> TYPE: DNA
<213> ORGANISM: Artificial Sequence
<220> FEATURE:
<223> OTHER INFORMATION: UL5 qPCR F primer

<400> SEQUENCE: 13
atgccgtagt cggcgtttat                                                  20
```

```
<210> SEQ ID NO 14
<211> LENGTH: 22
<212> TYPE: DNA
<213> ORGANISM: Artificial Sequence
<220> FEATURE:
<223> OTHER INFORMATION: UL5 qPCR R primer

<400> SEQUENCE: 14
cgagtttgtc gagtccattg ac                                              22

<210> SEQ ID NO 15
<211> LENGTH: 16
<212> TYPE: DNA
<213> ORGANISM: Artificial Sequence
<220> FEATURE:
<223> OTHER INFORMATION: UL5 FAM MGB primer

<400> SEQUENCE: 15
atggccagct ccgtag                                                     16
```